United States Patent
Du et al.

(10) Patent No.: US 12,194,040 B2
(45) Date of Patent: *Jan. 14, 2025

(54) FAK INHIBITOR AND DRUG COMBINATION THEREOF

(71) Applicant: HINOVA PHARMACEUTICALS INC., Sichuan (CN)

(72) Inventors: Wu Du, Sichuan (CN); Yu Li, Sichuan (CN); Kun Wen, Sichuan (CN); Xinghai Li, Sichuan (CN); Yuanwei Chen, Sichuan (CN)

(73) Assignee: HINOVA PHARMACEUTICALS INC., Sichuan (CN)

( * ) Notice: Subject to any disclaimer, the term of this patent is extended or adjusted under 35 U.S.C. 154(b) by 699 days.

This patent is subject to a terminal disclaimer.

(21) Appl. No.: 17/418,678

(22) PCT Filed: Dec. 24, 2019

(86) PCT No.: PCT/CN2019/128030
§ 371 (c)(1),
(2) Date: Jun. 25, 2021

(87) PCT Pub. No.: WO2020/135442
PCT Pub. Date: Jul. 2, 2020

(65) Prior Publication Data
US 2022/0125788 A1  Apr. 28, 2022

(30) Foreign Application Priority Data

Dec. 27, 2018 (CN) .......................... 201811614990.2

(51) Int. Cl.
*A61K 31/506* (2006.01)
*A61K 39/395* (2006.01)
*A61P 35/00* (2006.01)
*C07D 403/12* (2006.01)

(52) U.S. Cl.
CPC ........ *A61K 31/506* (2013.01); *A61K 39/3955* (2013.01); *A61P 35/00* (2018.01); *C07D 403/12* (2013.01); *C07B 2200/05* (2013.01)

(58) Field of Classification Search
CPC ...... A61K 31/501; A61K 47/26; A61K 47/40; A61K 47/46; A61P 21/00
USPC ..................................................... 514/55.05
See application file for complete search history.

(56) References Cited

U.S. PATENT DOCUMENTS

2011/0053968 A1   3/2011 Zhang

FOREIGN PATENT DOCUMENTS

| CN | 106146406 A | 11/2016 |
| CN | 110452229 A | 11/2019 |
| WO | WO-2008129380 A1 * | 10/2008 | .......... A61K 31/506 |
| WO | 2010144499 A2 | 12/2010 |
| WO | WO-2017004192 A1 * | 1/2017 | .......... A61K 31/337 |
| WO | 2017201043 A1 | 11/2017 |

OTHER PUBLICATIONS

Kaur et al. "Deuteration as a Tool for Optimization of Metabolic Stability and Toxicity of Drugs." Global Journal of Pharmacy & pharmacuetical Science vol. 1, Issue 4,. (Year: 2017).*
Zhang, Yinsheng; Development of deuterated drngs: past present and future; Progress in Pharmaceutical Sciences, vol. 41, No. 12, Dec. 31, 2017, pp. 902-918.
Lockley, W.J.S.; Hydrogen isotope labelling using iridium(I) dionates, Journal of Labelled Compounds and Radiopharmaceuticals, 53(11-12), 668-673; 2010.
Salen, Hesham et al.; Deuterium-Labeled Precursor Feeding Reveals a New pABA—Containing Meroterpenoid from the Mango Pathogen *Xanthomonas citri* pv. mangiferaeindicae, Journal of Natural Products, 79(6), 1532-1537; 2016.
Robberts, Walter Gregory et al.; Antitumor Activity and Pharmacology of a Selective Focal Adhesion Kinase Inhibitor, PF-562,271 Cancer Research. Mar. 15, 2008, 68(6), 1935-1944.

* cited by examiner

*Primary Examiner* — Yevgeny Valenrod
(74) *Attorney, Agent, or Firm* — NKL Law; Allen Xue

(57) ABSTRACT

A deuterated compound as represented by formula (I) or an optical isomer, a tautomer, a pharmaceutically acceptable salt, a prodrug, a hydrate, or a solvate thereof are presented. Compared with a compound before deuteration, the deuterated compound shows better pharmacokinetics, higher maximum plasma drug concentration, higher exposure, and longer half-life, and has more excellent metabolic performance. The deuterated compound can effectively inhibit FAK activity, and has good application prospect in preparation of FAK inhibitors and/or drugs for treating cancer. In addition, the use of the deuterated compound in combination with an anti-cancer drug (such as a PD-1 inhibitor) can achieve a synergistic effect, thereby significantly improving the tumor suppression effect, and providing a better choice for clinical cancer treatment.

(I)

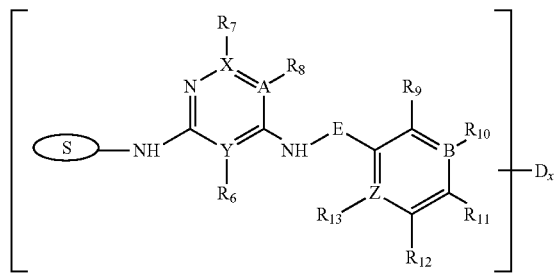

5 Claims, 1 Drawing Sheet

FAK INHIBITOR AND DRUG COMBINATION THEREOF

CROSS REFERENCES TO RELATED APPLICATIONS

The present application is a U.S. national stage entry of International Application No. PCT/CN2019/128030, filed Dec. 24, 2019, which claims the priority to the Chinese Patent application CN 201811614990.2 submitted to China National Intellectual Property Administration on Dec. 27, 2018 which is entitled "FAK INHIBITOR AND DRUG COMBINATION THEREOF". The entire contents of the prior application are incorporated herein by reference.

TECHNICAL FIELD

The present invention belongs to the field of medicinal chemistry, and specifically relates to an FAX inhibitor and a drug combination thereof.

BACKGROUND ART

Focal adhesion kinase (FAK) is a non-receptor tyrosine kinase in cells, which was first discovered in transfected V-Src chicken embryo fibroblasts. FAX has higher expression in most tissues, and its protein sequence has higher homology in many species (mouse, toad, human, etc.). FAK is the intersection of multiple signal transduction pathways in the cell, involved in tumor formation, proliferation, metastasis and apoptosis, cardiovascular disease and other biological processes. It is currently one of the anti-tumor targets that has received widespread attention.

Recent studies have found that FAK can be activated by a variety of factors, including integrins, C protein-coupled receptors, etc. At the same time, FAK regulates intracellular P53 and PI3K-AKT-mTOR signal pathways by kinase-dependent and non-kinase-dependent pathways, and is involved in the biological processes of tumor cell survival, proliferation, and metastasis. The initial attempt was to suppress the tumor by down-regulating the expression of FAK in tumor cells. By transfecting FAK with inactivated carboxyl end (FAK-CD), FAK is silenced, cell adhesion and proliferation are reduced, and the inhibitory effect on the growth of breast cancer cells is achieved in in vivo experiments. By transfecting a plasmid containing FAK-silenced RNA (FAK-siRNNA), cancer is suppressed in vivo. Simultaneously inhibiting the expression of FAK and FAK downstream signaling molecules (such as SRC) can enhance the anti-tumor effect.

Taking into account the important functions of FAK in tumor cells, the reliability of gene transfection and the safety of viral vectors, small molecule inhibitors based on the FAK signaling pathway have begun to appear, and good results have been achieved in recent years. At present, there are many FAK inhibitors as anti-tumor drugs, which are in the stage of preclinical research or clinical trials. As reported in the literature (the new anti-tumor target focal adhesion kinase FAK and the research progress of its inhibitors, Chen Ying, etc.), TAE226, also known as NVP-226, can block the connection site of FAK and ATP, as well as the phosphorylation sites of Y397 and Y861 in FAK, and play a role in the inhibition of FAK activity. However, there is still a need in the art to develop FAK inhibitors with better inhibitory activity or better pharmacodynamic properties.

Deuterated drugs mean part of the hydrogen atoms in the drug molecules are substituted with deuterium. Deuterium (D) is a stable isotope of hydrogen. Because the form and volume of deuterium in the drug are basically the same as hydrogen, some hydrogen atoms in the drug molecule are replaced by deuterium, but the activity of the drug molecule remains basically unchanged. In addition, since the mass of deuterium atoms is twice that of hydrogen, the vibrational zero-point energy of carbon-deuterium bonds (CD) is lower than that of carbon-hydrogen bonds (CH), and thus the carbon-deuterium bond is more stable. Replacing part of the hydrogen atoms in drug molecules with deuterium can delay the degradation process of the drug, make the deuterated drug act longer in the body, and achieve the purpose of changing the metabolism speed or metabolic pathway of drug, thereby improving the pharmacokinetics and reducing the metabolic toxicity of the drug. In view of the important use of FAK inhibitors in the field of tumor treatment and their limitations, combining them with deuterated drug technology, discovering new molecular entities, reducing their impact on liver and kidney function, and improving the safety and effectiveness of drug is a research trend that promotes the further development of this type of drugs, having great application values.

The combined use of drugs is an effective way to improve the therapeutic effects of drugs. There is no report on the combined use of deuterated FAK inhibitors with other anti-cancer drugs or anti-cancer methods.

CONTENT OF THE INVENTION

In order to solve the above-mentioned problems, the present invention provides a deuterated compound and its use as a FAK inhibitor, as well as a regimen for the combined use of the deuterated compound mentioned above with other anti-cancer drugs.

The present invention provides compound of formula (I) or an optical isomer, a tautomer, a pharmaceutically acceptable salt, a prodrug, a hydrate, or a solvate thereof:

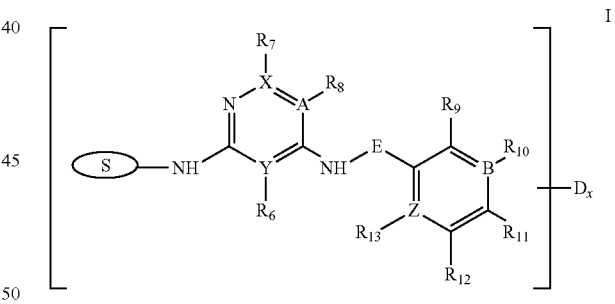

wherein, ring S is selected from aromatic ring or five-membered heterocyclic ring; each of A, B, X, Y, and Z is independently selected from C or N; E is none or methylene;

and/or, $R_6$ is selected from H or none; $R_7$ is selected from H, N, or none; $R_8$ is selected from haloalkyl or halogen, or $R_7$ and $R_8$ are linked to form a ring;

and/or, $R_9$ is selected from —NMeSO$_2$Me, —CONHOMe, —CONHMe, amide, hydrogen or none; $R_{10}$ is selected from H or none; $R_{11}$ is selected from —NHSO$_2$Me, halogen, substituted piperazine or hydrogen, and the substituent in the piperazine is ethanol group; $R_{12}$ is selected from —SO$_2$Me or H; $R_{13}$ is selected from —CONHMe, —CONHOMe, N-alkylsulfonamide, H or none, or $R_{11}$ and $R_{13}$ are linked to form a ring;

Dx in formula (I) represents that the hydrogen on at least one carbon atom of the compound in the brackets is substituted by deuterium, and x is an integer of ≥1.

Preferably, said compound has a structure of formula (I-A):

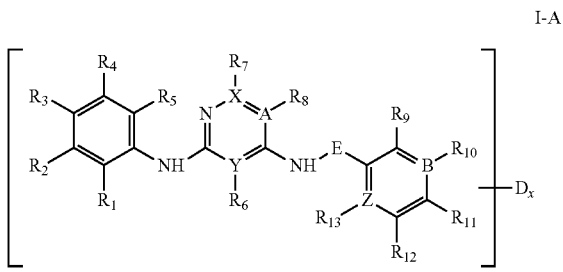

I-A wherein, each of A, B, X, Y, and Z is independently selected from C or N; E is none or methylene;

$R_1$ and $R_5$ are selected from H or methoxy; $R_2$ and $R_4$ are selected from H or methoxy; $R_3$ is selected from H, —CONHMe, alkoxyamide, morpholine, methoxy, ethylamine or sulfonamide, or $R_2$ and $R_3$ are linked to form a ring, or $R_3$ and $R_4$ are linked to form a ring;

and/or, $R_6$ is selected from H or none; $R_7$ is selected from H, N, or none; $R_8$ is selected from haloalkyl or halogen, or $R_7$ and $R_8$ are linked to form a ring;

and/or, $R_9$ is selected from —NMeSO$_2$Me —CONHOMe, —CONHMe, amide, hydrogen, or none; $R_{10}$ is selected from H or none; $R_{11}$ is selected from —NHSO$_2$Me, halogen, substituted piperazine or hydrogen, and the substituent in the piperazine is ethanol group; Rn is selected from —SO$_2$Me or H; $R_{13}$ is selected from —CONHMe, N-alkylsulfonamide, H or none, or $R_{11}$ and $R_{13}$ are linked to form a ring, or $R_{13}$, $R_3$, and $R_4$ are linked to form a ring Dx in formula (I-A) represents that the hydrogen on at least one carbon atom of the compound in the brackets is substituted by deuterium, and x is an integer of ≥1.

Preferably, said compound has a structure of formula (I-B):

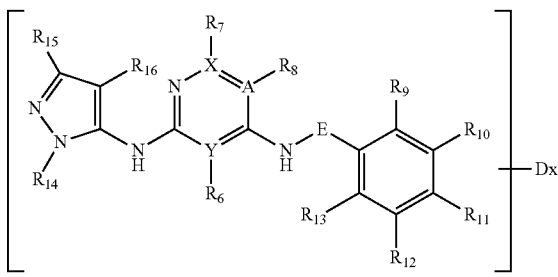

I-B wherein, A, X and Y are selected from C or N; E is none;

Each of $R_{14}$, $R_{15}$ and $R_{16}$ is independently selected from H, $C_{1-6}$ alkyl, $C_{3-6}$ cycloalkyl, methyl, ethyl or isopropyl;

and/or, $R_6$ is H; $R_7$ is H; $R_8$ is halogen;

$R_9$ and $R_{13}$ are selected from —CONHOMe, —CONHMe or H; $R_{10}$ and $R_{12}$ are H;

$R_{11}$ is selected from halogen, H or substituted piperazine, and the substituent in the piperazine is ethanol group;

Dx in formula (I-B) represents that the hydrogen on at least one carbon atom of the compound in the brackets is substituted by deuterium, and x is an integer of ≥1.

Preferably, said compound has a structure of formula (I-C):

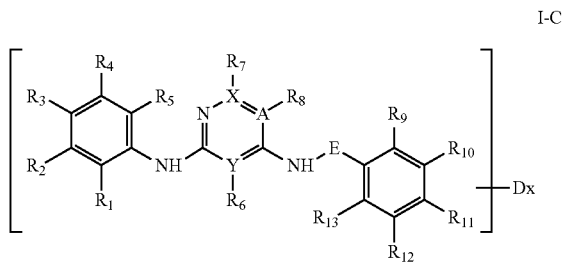

I-C wherein, A, X and Y are selected from C or N; E is methylene or none;

$R_9$ and $R_{13}$ are selected from H, —NMeSO$_2$Me, —CONHOMe, or —CONHMe; $R_{10}$ and $R_{12}$ are H;

$R_{11}$ is selected from H, substituted piperazine or halogen, and the substituent in the piperazine is ethanol group;

and/or, $R_6$ is selected from H; $R_7$ is selected from H; $R_8$ is selected from haloalkyl or halogen; or $R_7$ and $R_8$ are linked to form a ring;

and/or, $R_1$, $R_4$, and $R_5$ are selected from H or methoxy; $R_2$ is selected from H or methoxy; $R_3$ is selected from H, —CONHMe, alkoxyamide, morpholine, methoxy, ethylamine or sulfonamide; or $R_2$ and $R_3$ are linked to form a ring;

Dx in formula (I-C) represents that the hydrogen on at least one carbon atom of the compound in the brackets is substituted by deuterium, and x is an integer of ≥1.

Preferably, said compound has a structure of formula (I-D):

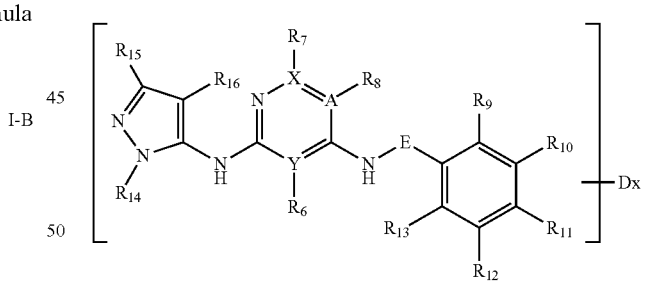

I-D wherein, $R_9$ and $R_{13}$ are selected from —CONHOMe, —CONHMe or H; $R_{10}$ and $R_{12}$ are H; $R_{11}$ is selected from halogen, H or substituted piperazine, and the substituent in the piperazine is ethanol group;

A, X and Y are selected from C or N; E is none;

and/or, $R_6$ is selected from H; $R_7$ is selected from H; $R_8$ is halogen;

and/or, $R_{14}$ is selected from methyl, ethyl or isopropyl; $R_{15}$ is selected from methyl or H; $R_{16}$ is H;

Dx in formula (I-D) represents that the hydrogen on at least one carbon atom of the compound in the brackets is substituted by deuterium, and x is an integer of ≥1.

Preferably, said compound has a structure of formula (I-E):

I-E

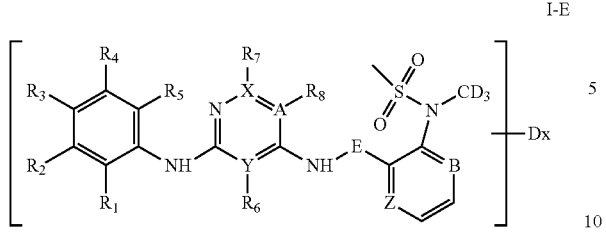

wherein, B and Z are selected from C or N; E is methylene; Y is N; X and A are C;
and/or, R₆ is none, R₇ is H; R₈ is haloalkyl;
and/or, R₁ and R₂ are H; R₃ is —CONHMe; R₄ is H; or R₃ and R₄ are linked to form a ring;
Dx in formula (I-E) represents that the hydrogen on at least one carbon atom of the compound in the brackets is substituted by deuterium, and x is an integer of ≥1.

Preferably, said compound has a structure of formula (I-F):

I-F

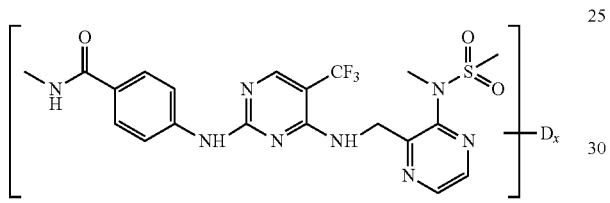

wherein, Dx in formula (I-F) represents that the hydrogen on at least one carbon atom of the compound in the brackets is substituted by deuterium, and x is an integer of ≥1.

Preferably, said compound has a structure of formula (I-G):

I-G

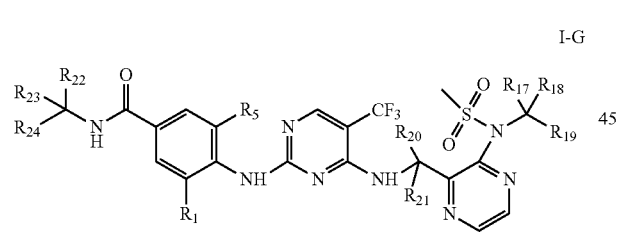

wherein, one or more of R₁, R₅, R₁₇, R₁₈, R₁₉, R₂₀, R₂₁, R₂₂, R₂₃, and R₂₄ is substituted by deuterium. Preferably, said compound is selected from but not limited to one of the following compounds substituted with deuterium:

1

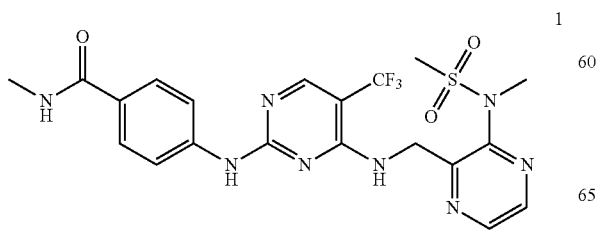

2

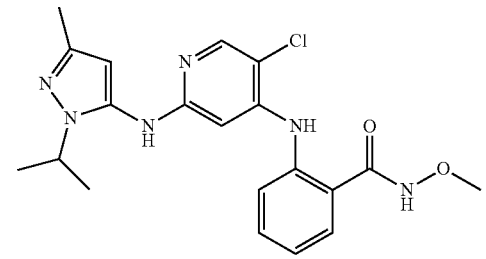

3

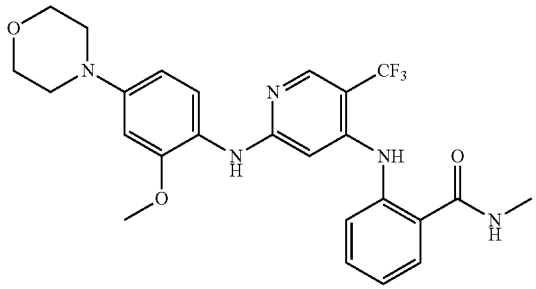

4

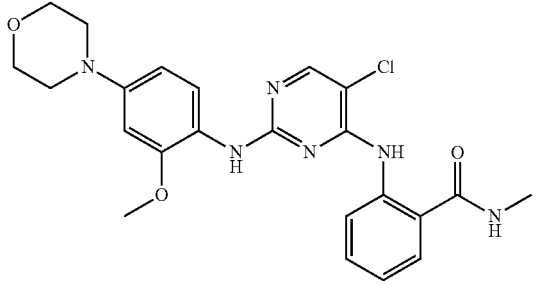

5

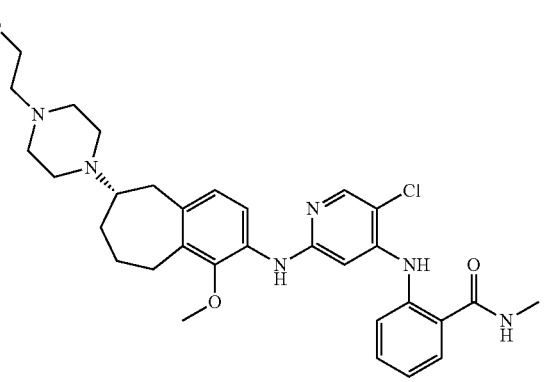

6

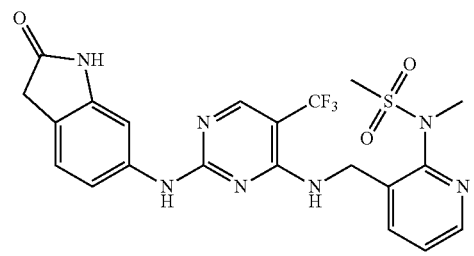

-continued
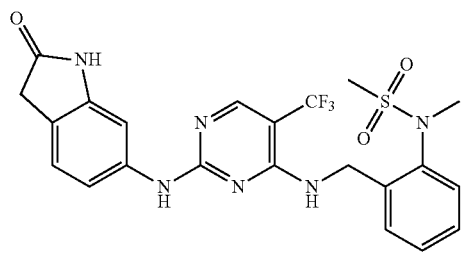
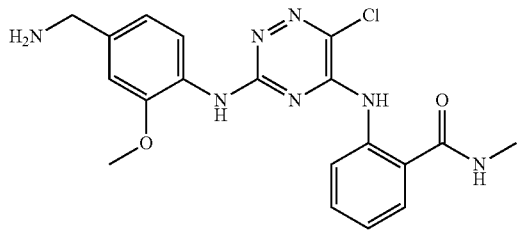
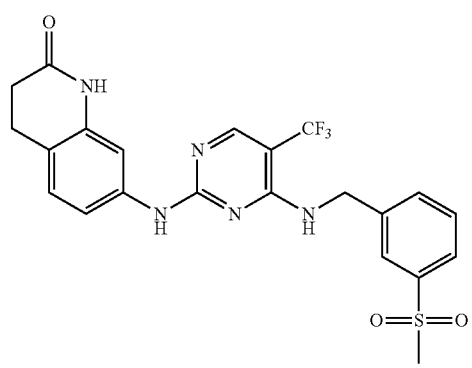
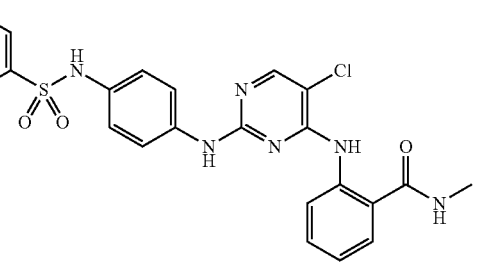
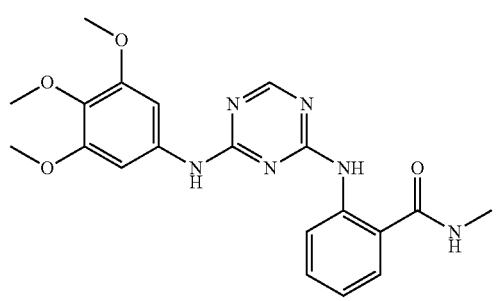
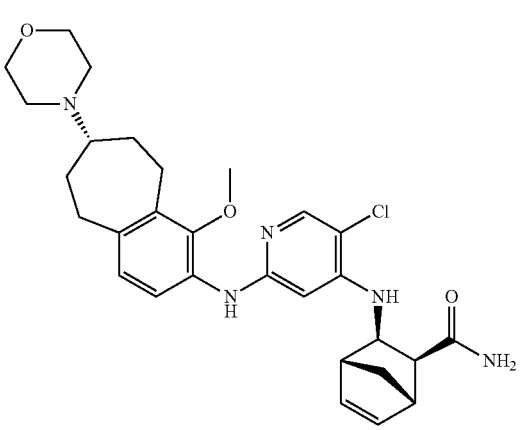
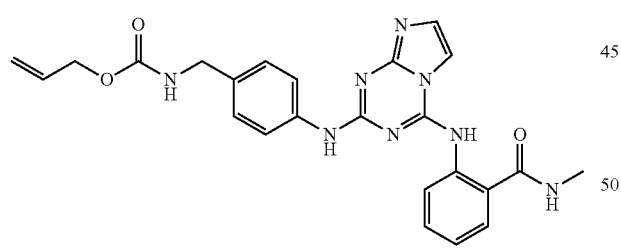
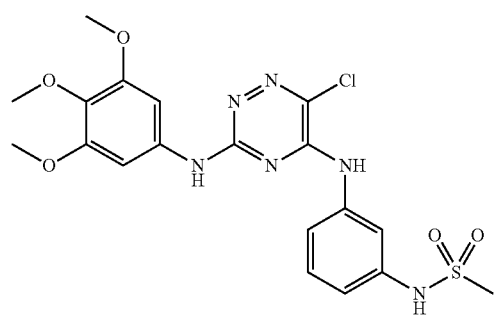
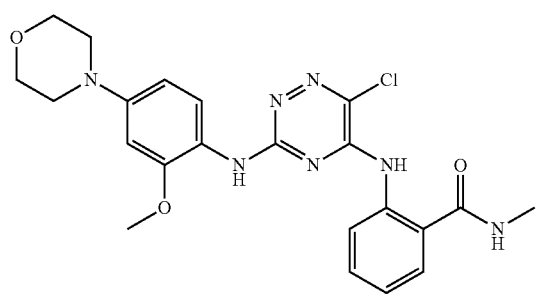
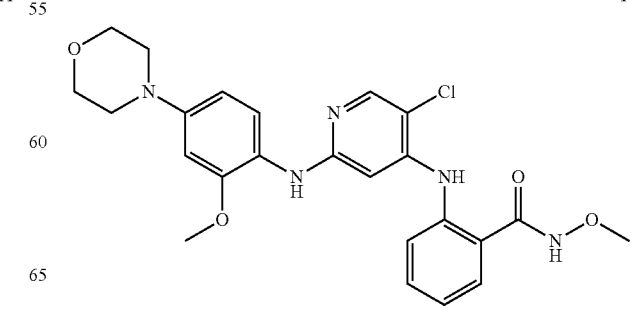

17
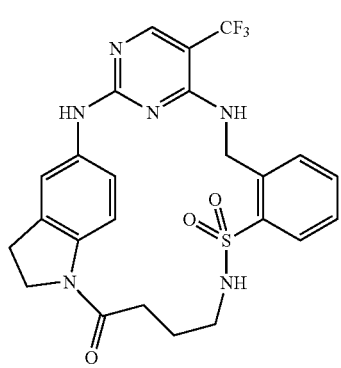
18
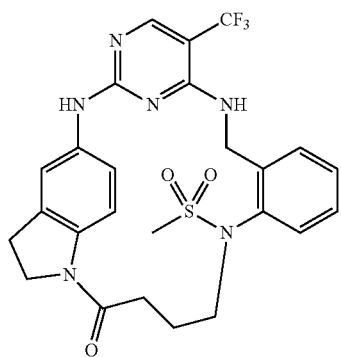
19
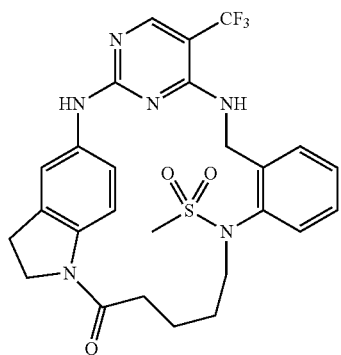
20
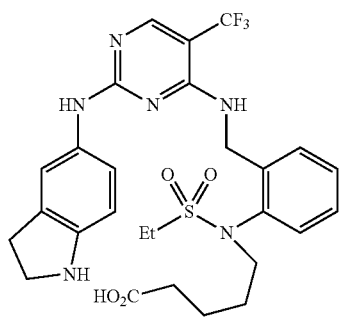
21
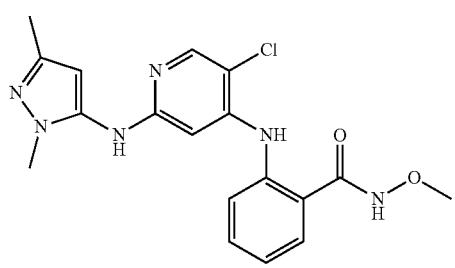
22
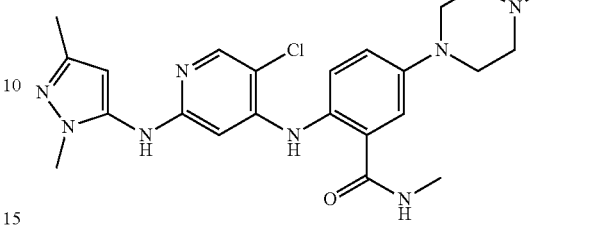
23
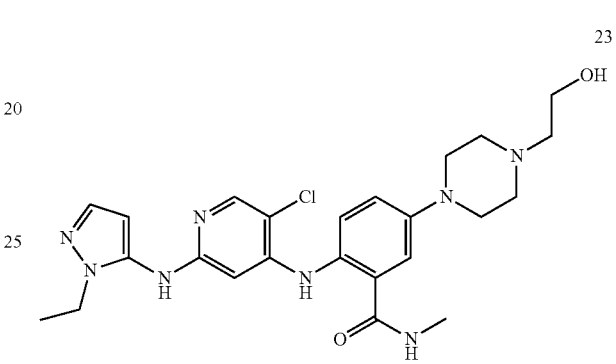
24
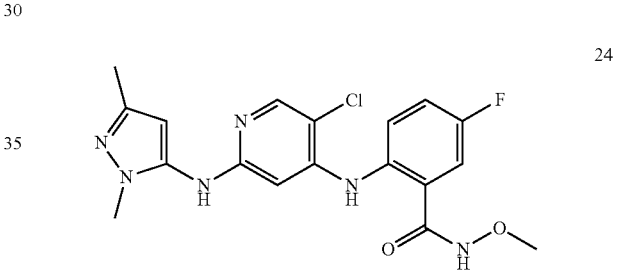
Preferably, said compound is selected from but not limited to one of the following compounds or one of the following compounds substituted with deuterium
25
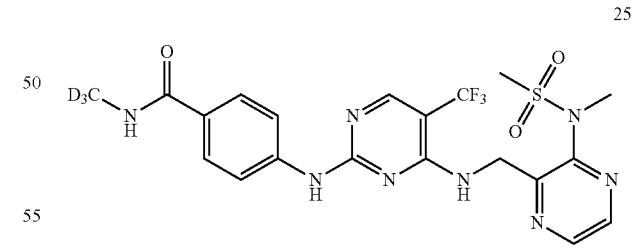
26
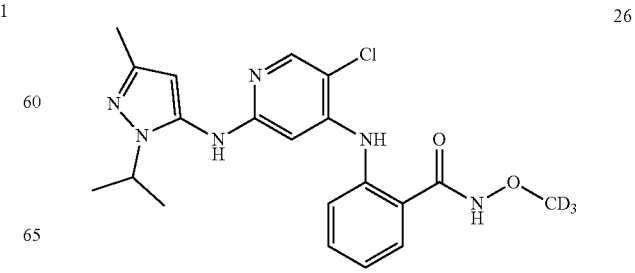

-continued
27
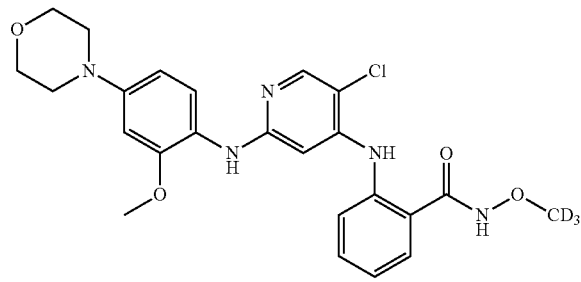
28
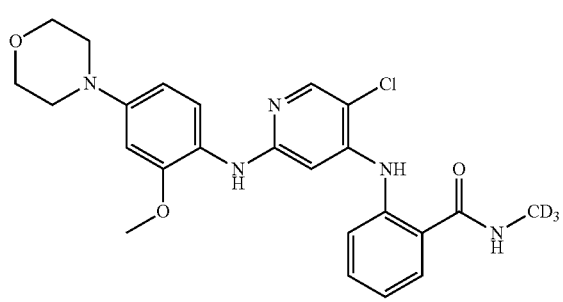
29
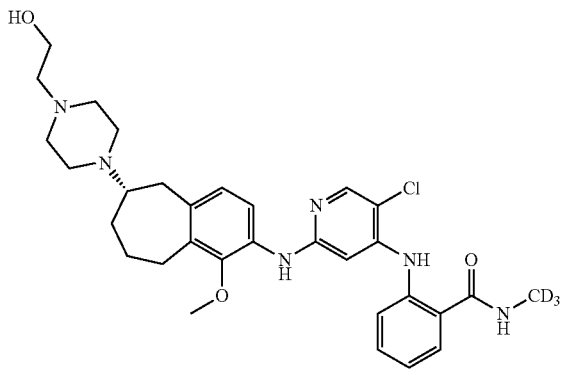
30
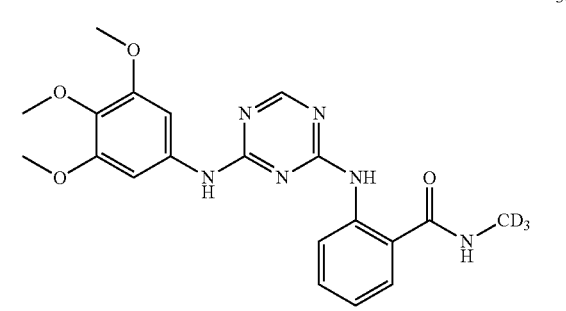
31
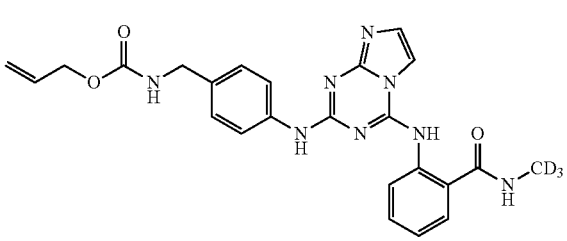
-continued
32
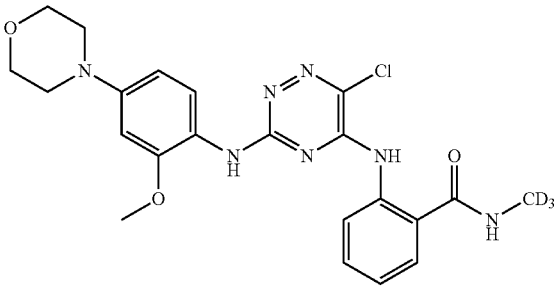
33
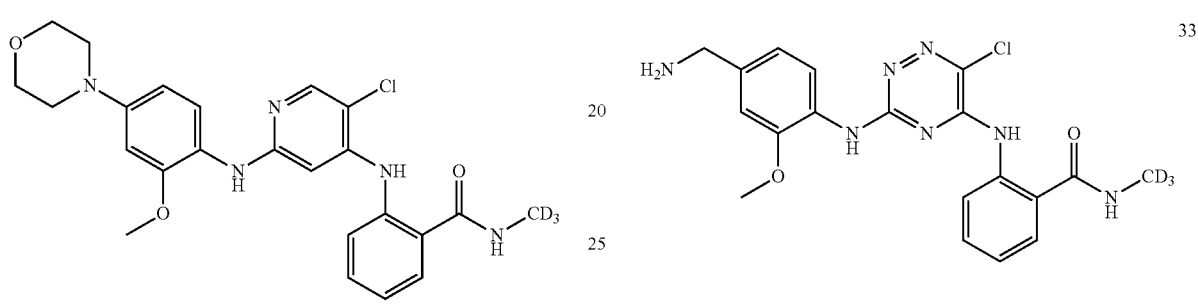
34
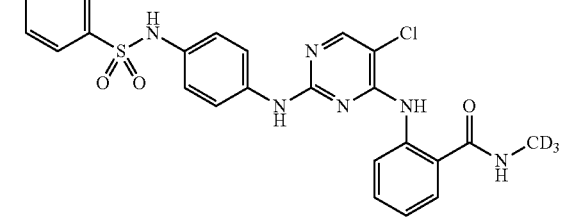
35
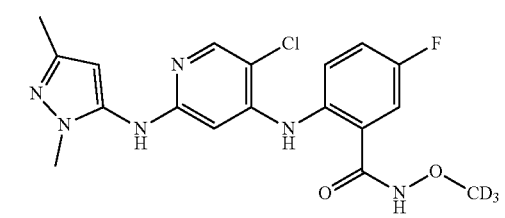
36
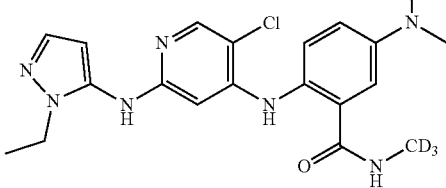

37
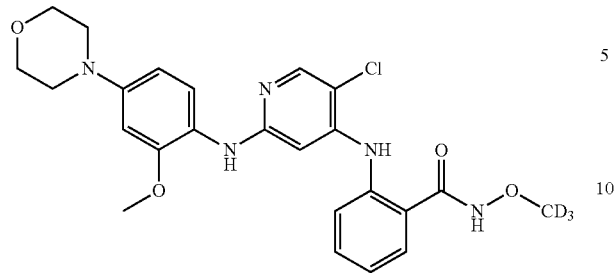
38
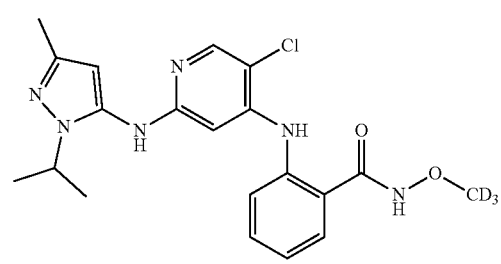
39
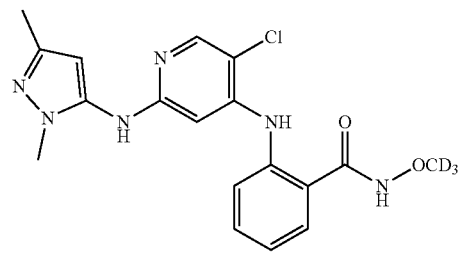
40
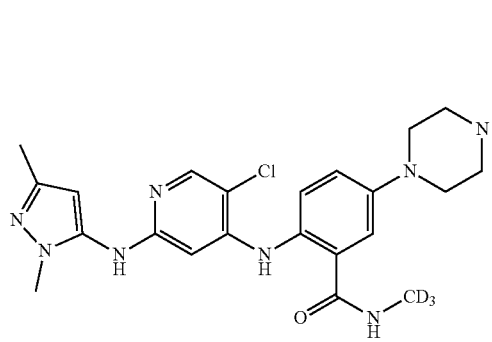
41
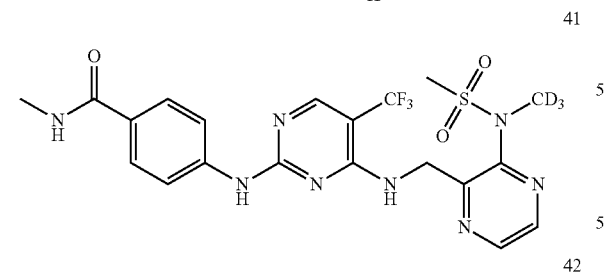
42
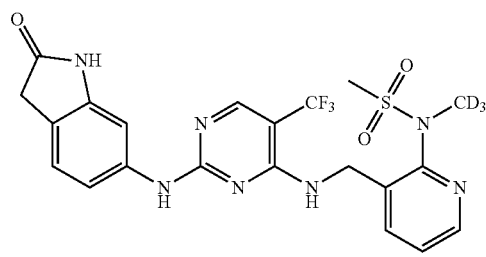
43
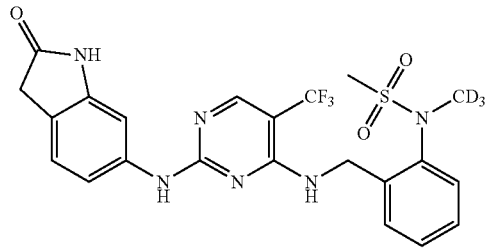
44
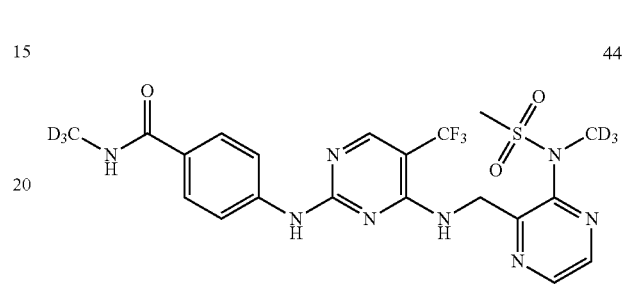
45
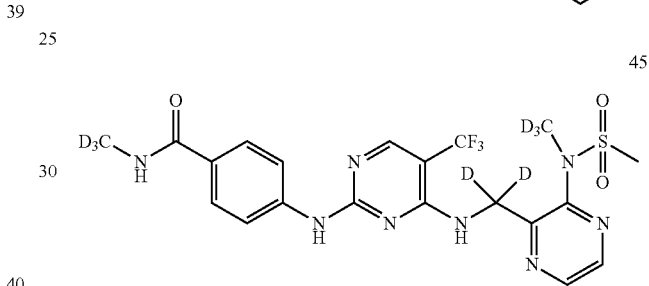
46
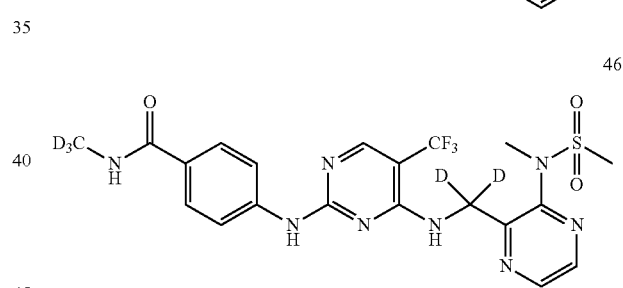
47
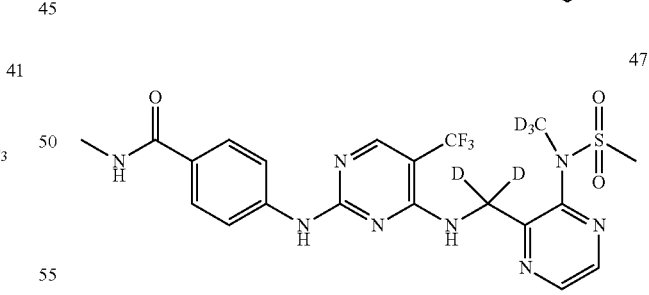
48
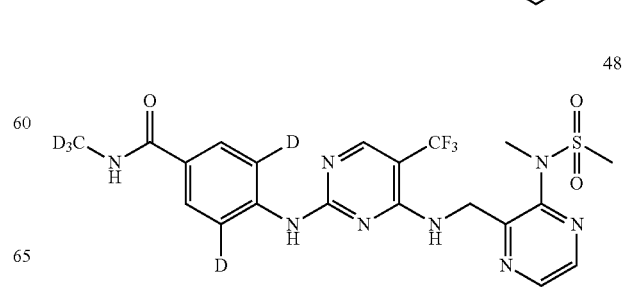

The present invention also provides the use of the compound mentioned above or an optical isomer, a tautomer, a pharmaceutically acceptable salt, a prodrug, a hydrate, or a solvate thereof in the preparation of an FAK inhibitor; preferably, the FAK inhibitor is a drug for the treatment of cancer.

Wherein, said cancer is solid tumors;

The solid tumors include mesothelioma, pancreatic cancer, soft tissue tumors, metastases, non-solid cancers, sarcomas, adenocarcinoma, lung cancer, breast cancer, lymphoma, gastrointestinal cancer, genitourinary system cancer, prostate cancer, and ovarian cancer; the gastrointestinal cancer includes colon cancer; the genitourinary system cancer includes kidney, urothelial or testicular tumors; and the ovarian cancer includes advanced ovarian cancer;

The mesothelioma includes neurofibromas, kidney cancer, lung cancer, small cell lung cancer, non-small cell lung cancer, KRAS mutant non-small cell lung cancer, liver cancer, thyroid cancer, breast cancer, nervous system tumors, schwannona, meningioma, neuroma, adenoid cystic carcinoma, ependymoma, ependymal tumors, malignant pleura, malignant pleural mesothelioma, triplet tumor, negative breast cancer, non-hematological malignancy, melanoma, colorectal carcinoma, leukemia, adenocarcinoma, solid tumor;

The melanoma includes locally advanced melanoma, melanoma caused by locally mutated N-Ras, metastatic malignant skin melanoma; the colorectal cancer includes metastatic colorectal cancer; and the leukemia includes acute myelogenous leukemia; the adenocarcinoma includes adenocarcinoma; and the solid tumor includes locally advanced solid tumor, metastatic solid tumor, and hepatocellular carcinoma.

The present invention further provides a drug combination for the treatment of tumors, that contains the compound mentioned above and an anticancer drug in the same or different specification unit preparations for simultaneous or separate administration, as well as a pharmaceutically acceptable carrier.

The anti-cancer drug is a drug for immunotherapy, a drug for chemotherapy or a drug for radiation therapy.

The immunotherapeutic drugs are selected from checkpoint inhibitors, PD-1 inhibitors, PD-L1 inhibitors, antibodies inhibiting CTLA-4, antibodies inhibiting TIM3, antibodies inhibiting LAG3, antibodies inhibiting TIGIT, antibodies blocking checkpoint targets, costimulatory antibodies, or cells for CAR-T therapy.

Said PD-1 inhibitor or PD-L1 inhibitor includes but is not limited to: nivolumab, CT-011; AMP-224, pembrolizumab, pidilizumab, MK-3475, BMS936559, MEDI4736, MSB001071 8C, MPDL-3280A, SHR-1210, IB1308, BGB-A317, JS001, GLS-010, GB226 Geptanolimab, HLX10, AK103, AK104, AK105, AK112, SSI-361, JY034, KN035, SHR1316, TQB2450, KL-A167, CS1001, STI-A1014, JS003, AK106, HLX-09, mPD-1 antibody;

The antibodies blocking checkpoint targets include IMP321 and MGA271;

The costimulatory antibody includes anti-4-1BB antibody, anti-OX40 antibody, anti-GITR antibody, anti-CD27 antibody, and anti-CD40 antibody.

Said chemotherapeutic drugs are toxic drugs, alkylating drugs, anti-metabolic drugs, antibiotics, hormone therapy drugs, anticancer drugs of natural product, topoisomerase inhibitor drugs, immune drugs, complex platinum drugs, kinase inhibitors, anti-proliferative drugs, antibodies, interferons, or drugs that regulate androgen signaling pathways.

Said toxic drugs include but are not limited to gemcitabine, paclitaxel, and docetaxel;

Said kinase inhibitors include but are not limited to MEK kinase inhibitors, cMet inhibitors, VEGFR2 inhibitors, and EGFR inhibitors;

Said drugs that regulate androgen signaling pathways include but are not limited to: androgen synthesis inhibitors, CYP17A inhibitors, androgen receptor inhibitors, BET inhibitors, BRD4 inhibitors, RORγ inhibitors, CBP/P300 inhibitors, BMX inhibitors, PARP inhibitors; preferably, the androgen receptor inhibitors include but are not limited to: Enzalutamide, Apalutamide, Bicalutamide, Abiraterone, ODM-201, EPI-001, ONC1-13B, EM-5854, JNJ-63576, TAS-3681, HC-1119, Prokrutamide, SHR3680.

The present invention further provides the use of the drug combination mentioned above in the preparation of drugs for treatment of cancers.

Wherein, said cancer is solid tumors;

The solid tumors include mesothelioma, pancreatic cancer, soft tissue tumors, metastases, non-solid cancers, sarcomas, adenocarcinoma, lung cancer, breast cancer, lymphoma, gastrointestinal cancer, genitourinary system cancer, prostate cancer, and ovarian cancer; the gastrointestinal cancer includes colon cancer; the genitourinary system cancer includes kidney, urothelial or testicular tumors; and the ovarian cancer includes advanced ovarian cancer;

The mesothelioma includes neurofibromas, kidney cancer, lung cancer, small cell lung cancer, non-small cell lung cancer, KRAS mutant non-small cell lung cancer, liver cancer, thyroid cancer, breast cancer, nervous system tumors, schwannoma, meningioma, neuroma, adenoid cystic carcinoma, ependymoma, ependymal tumors, malignant pleura, malignant pleural mesothelioma, triplet tumor, negative breast cancer, non-hematological malignancy, melanoma, colorectal carcinoma, leukemia, adenocarcinoma, solid tumor;

The melanoma includes locally advanced melanoma, melanoma caused by locally mutated N-Ras, metastatic malignant skin melanoma; the colorectal cancer includes metastatic colorectal cancer; and the leukemia includes acute myelogenous leukemia; the adenocarcinoma includes adenocarcinoma; and the solid tumor includes locally advanced solid tumor, metastatic solid tumor, and hepatocellular carcinoma.

In the present invention, "alkyl" includes straight or branched alkyl.

In the present invention, the term "compound of the present invention" means the compound of formula (I). The term also includes various crystal forms, pharmaceutically acceptable salts, hydrates or solvates, optical isomers, tautomers, and prodrugs of the compound of formula (I).

In the present invention, the term "pharmaceutically acceptable salt" means a salt suitable for use as a medicine that is formed by a compound of the present invention and an acid or a base. Pharmaceutically acceptable salts include inorganic salts and organic salts. A preferred class of salts are the salt of the compound of the present invention with alkali metal. Alkali metals suitable for salt formation include but are not limited to: lithium, sodium, potassium, calcium, magnesium and the like.

The administration way of the compound or the pharmaceutical composition according to the present invention is not particularly limited, and typical administration ways include (but are not limited to): oral, parenteral (intravenous, intramuscular, or subcutaneous), and topical administration.

The present invention provides a deuterated compound, and compared with the compound before deuteration, it shows better pharmacokinetics, higher maximum plasma concentration, higher exposure and longer half-life, and has more excellent metabolic performance. Moreover, the deuterated compound of the present invention can effectively inhibit the activity of FAK, and has a very good application prospect in the preparation of F/AK inhibitors and/or drugs for treatment of cancer. At the same time, the use of the deuterated compound of the present invention in combination with anti-cancer drugs (such as PD-1 inhibitors) can play a synergistic effect, significantly improve the inhibitory effect on tumors, and provide a better choice for clinical treatment of cancer.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Figure 1:
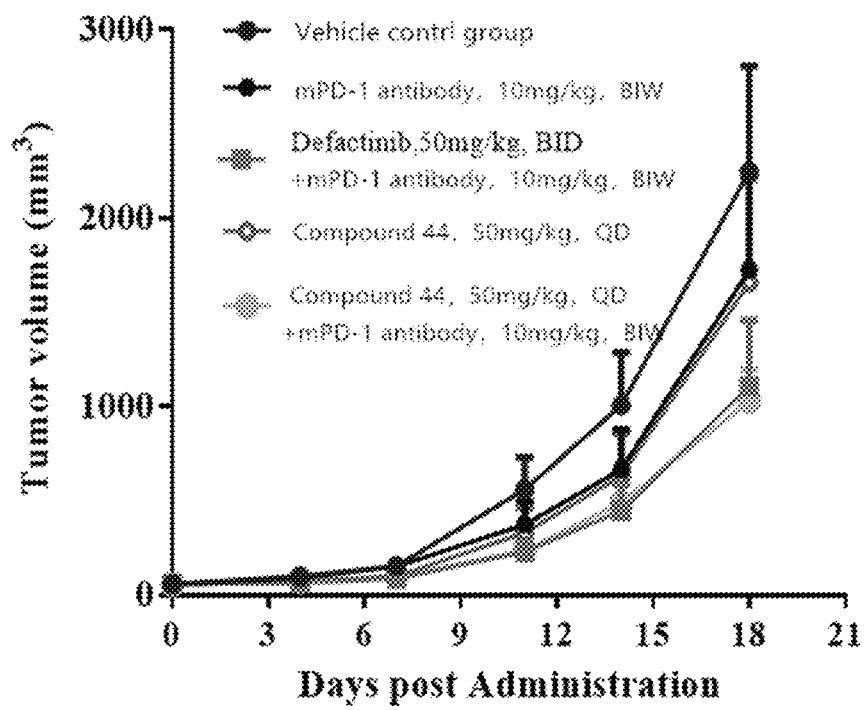
FIG. 1. The pharmacodynamic experiment of the deuterated compound according to the present invention on the MC38 tumor animal model.

The starting materials and equipment used in the present invention can be obtained by purchasing commercially available products.

Example 1 Synthesis of N-trideuteromethyl-4-((4-(((3-(N-methanesulfonamido) pyrazin-2-yl)methyl) amino)-5-(trifluoromethyl)pyrimidin-2-yl)amino) benzamide (Compound 25)

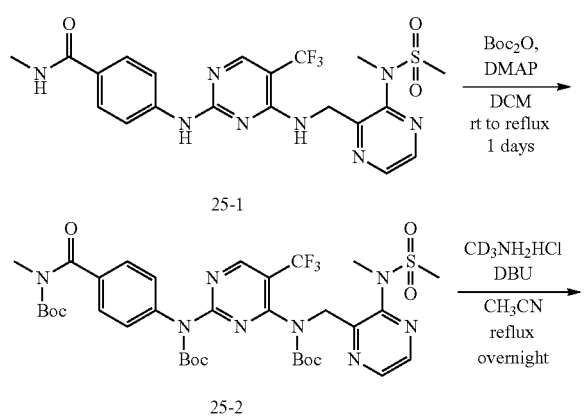

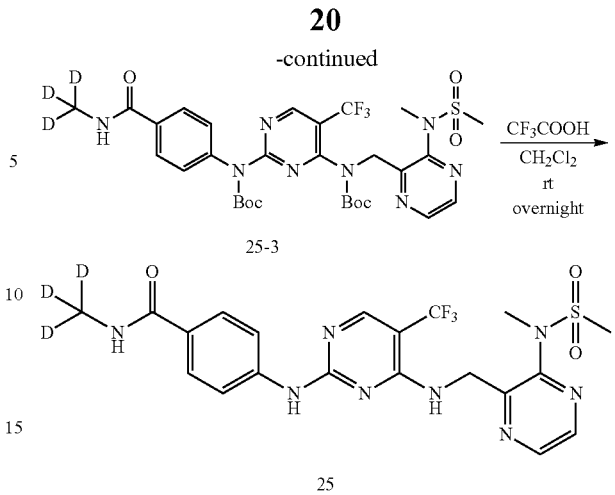

Step 1: Synthesis of Compound 25-2

25-1 (200 mg, 0.39 mmol) and DMAP (1.29 g, 10.57 mmol) were added in 10 mL of dichloromethane, to which was then added (Boc)$_2$O (1.71 g, 7.83 mmol) dropwise. The system was refluxed in an oil bath for 24 h. The next day, the reaction was cooled to room temperature, to which were added dichloromethane and 0.1 N HCl solution. The mixture was extracted, and then stood to separate the layers. The organic phase was washed with saturated brine, dried over anhydrous sodium sulfate, filtered by suction, and evaporated to remove the solvent. The crude product was separated by column chromatography, to provide an off-white solid 25-2 (136 mg, yield: 42.8%). MS (M+1): 811.2.

Step 2: Synthesis of Compound 25-3

25-2 (136 mg, 0.17 mmol) and deuterated methylamine hydrochloride (189 mg, 2.68 mmol) were added to 5 mL of acetonitrile, and the mixture was stirred at room temperature. Then, DBU (613 mg, 4.03 mmol) was added, and gradually dissolved until the reaction solution became clear. After that, the system was placed in an oil bath to reflux and react overnight. The next day, the reaction was cooled to room temperature, and rotary evaporated to remove the solvent. Dichloromethane and 0.1 N HCl solution were added to the system, and the reaction was stirred vigorously and stood for separation. The organic phase was respectively washed with purified water and saturated brine, dried with anhydrous sodium sulfate, and rotary evaporated to remove the solvent. The residue was separated and purified by Pre-TLC (PE/EA=2:1), to obtain a white solid 25-3 (42 mg, yield 35.3%). MS (M-Boc+1): 614.2.

Step 3: Synthesis of Compound 25

25-3 (42 mg, 0.06 mmol) was added to 2 mL of dichloromethane and stirred at room temperature (unable to dissolve and became clear), to which 0.1 mL of trifluoromethanesulfonic acid was then added. The system gradually became transparent and clear, and the mixture was allowed to stir and react overnight at room temperature. The next day, the solvent was removed by rotary evaporation, and ethyl acetate and saturated NaHCO$_3$ solution were added to the system. The resultant mixture was stirred vigorously, and then left to stand for separation. The pH value of the aqueous phase was detected to be about 7 to 8. The organic layer was washed twice with water and saturated brine, respectively, and dried with anhydrous sodium sulfate. The solvent was removed by rotary evaporation to obtain a white solid compound 25 (24 mg, yield: 80.0%).

$^1$HNMR (400 Hz, DMSO-d$_6$): δ 9.863 (1H, s), 8.688 (1H, d, J=2.4 Hz), 8.581 (1H, d, J=2.8 Hz), 8.316 (1H, s), δ 8.180 (1H, s), 7.665-7.594 (4H, dd, J$_1$=19.6 Hz, J$_2$=8.8 Hz), 7.476-7.450 (1H, t, J=5.2 Hz), 5.001 (2H, d, J=4.8 Hz), 3.221 (3H, s), 3.199 (3H, s). LC-MS (M+H$^+$): 514.2.

Using starting materials corresponding to the compound and a preparation method similar to that of compound 25, compounds 26 to 40 were prepared.

Example 2 Synthesis of N-methyl-4-((4-(((3-(N-trideuteromethylmethanesulfonamido) pyrazin-2-yl)methyl)amino)-5-(trifluoromethyl)pyrimidin-2-yl)amino)benzamide (Compound 41)

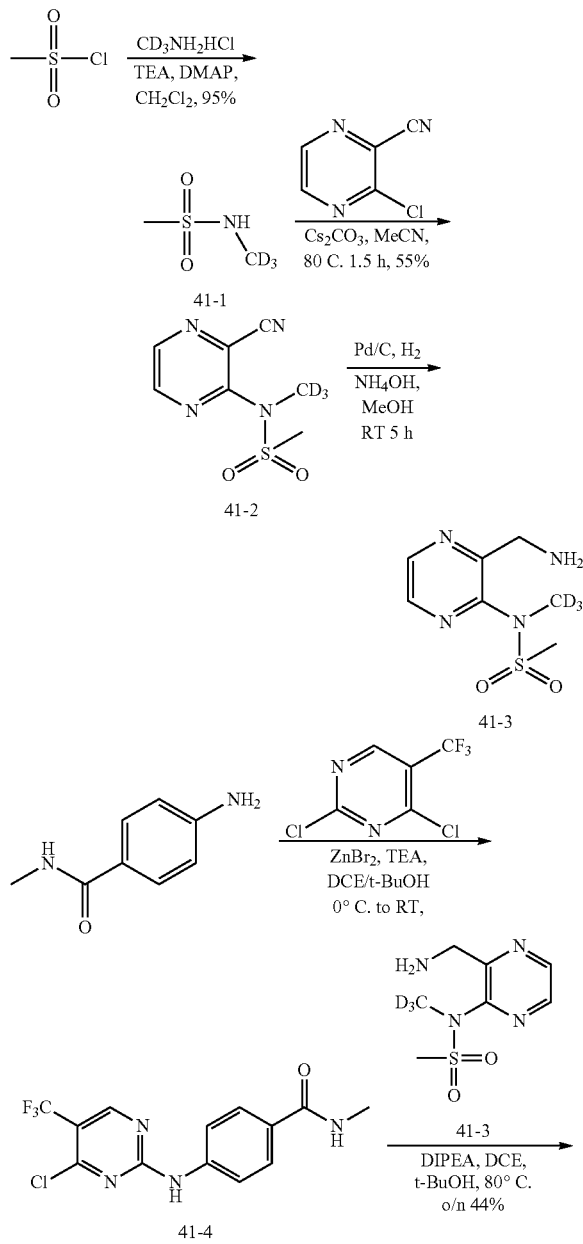

Step 1: Synthesis of N-trideuteromethylmethanesulfonamide (Compound 41-1)

Deuterated methylamine hydrochloride (7.75 g, 109.99 mmol) was placed in a 250 mL single-neck round bottom flask, and dichloromethane (120 mL) was added at the same time. The mixture was stirred at room temperature. Subsequently, the system was placed in an ice water bath to cool down and stirred. After 15 min, triethylamine (21.73 g, 214.75 mmol) and DMAP (128 mg, 1.05 mmol) were successively added. Then, the system was further stirred for 10 min in an ice water bath. After that, methanesulfonyl chloride (12.0 g, 104.76 mmol) was added to the system, and then the ice bath was removed. The system was allowed to stir and react at room temperature overnight. The next day, the reaction was completed by TLC detection, and the system was subjected to filtration. The filter cake was rinsed with ethyl acetate several times, the filtrate was combined, and the solvent was removed by rotary evaporation. Then, ethyl acetate (90 mL) was added to the system and stirred vigorously for 10 min. Afterwards, the system was subjected to the suction filtration again, and the filter cake was also rinsed with ethyl acetate several times in small amounts. The filtrate was combined and concentrated in vacuo to obtain N-trideuteromethylmethanesulfonamide (11.16 g) as colorless and transparent oily liquid, which was directly used in the next step, without further purification. Yield: 94.9%. LC/MS (ESI+): m/z 113.3 [M+H]$^+$ (calcd for C$_2$H$_4$D$_3$NO$_2$S, 113.1).

Step 2: Synthesis of N-(3-cyanopyrazin-2-yl)-N-trideuteromethylmethanesulfonamide (Compound 41-2)

N-Trideuteromethylmethanesulfonamide (6.0 g, 53.54 mmol) and 2-chloro-3-cyanopyrazine (6.23 g, 44.62 mmol) were placed in a 500 mL single-neck round bottom flask, and at the same time, acetonitrile (300 mL) was added. The resultant mixture was stirred at room temperature. Subsequently, cesium carbonate (24.71 g, 75.85 mmol) was added to the system. Then, the system was moved to an oil bath at 80° C., and the reaction was further heated and stirred. After 1.5 h, the sample was collected and subjected to TLC. TLC showed that the raw materials have disappeared. Heating was removed, and the system was allowed to cool to room temperature naturally, followed by filtration. The filter cake was rinsed with acetonitrile in small amounts for several times, and then the filtrate was combined. The solvent was removed by rotary evaporation. After that, ethyl acetate (150 mL) and water (150 mL) were added to the system. The resultant mixture was stirred vigorously, and stood still to separate the layers. The aqueous phase was back-extracted with ethyl acetate (50 mL*3). The organic phases were combined, washed successively with purified water (30 mL×3) and saturated brine (30 mL), dried with anhydrous sodium sulfate, and concentrated in vacuo to obtain a crude product, which was separated and purified by column chromatography to obtain N-(3-cyanopyrazin-2-yl)-N-deuteromethylmethanesulfonamide (5.29 g) as pale brown-red oily liquid. Yield: 55.1%. LC/MS (ESI+): m/z 233.1 [M+H$_2$O] (calcd for C$_7$H$_5$D$_3$N$_4$O$_2$S [M+H]$^+$, 216.1) $^1$H NMR (400 MHz, DMSO-d$_6$) δ 8.65-8.63 (dd, J=6.0, 2.4 Hz, 211), 3.26 (s, 311).

Step 3: Synthesis of N-(3-(aminomethyl)pyrazin-2-yl)-N-trideuteromethylmethanesulfonamide (Compound 41-3)

N-(3-Cyanopyrazin-2-yl)-N-deuteromethylmethanesulfonamide (2.0 g, 9.30 mmol) was weighed and placed in a 500 mL single-neck round bottom flask, to which was added methanol (270 mL), and then the mixture was stirred at room temperature until the reactions were dissolved and the solution became clear. Subsequently, wet palladium carbon (1 g) and ammonia water (20 mL) were added to the system. After that, the system was evacuated, and the purge process of argon gas was repeated 5 times to ensure an inert gas atmosphere in the system. The system was replaced with hydrogen again, and after that, the system was still stirred and reacted at room temperature. After 5 h, the sample was collected and subjected to TLC. TLC showed that the raw materials had been consumed. The reaction was terminated, and the hydrogenation unit was removed. The system was subjected to the suction filtration, and the filter cake was repeatedly eluted with methanol several times. The filtrate was combined, and the solvent was removed by rotary evaporation. The residual water in the system was removed by multiple times of rotary evaporation with methanol, to obtain N-(3-(aminomethyl)pyrazin-2-yl)-N-deuteromethylmethanesulfonamide as a light yellow-brown transparent oily liquid, which was directly used in the next step without further purification. LC/MS (ESI+): m/z 220.1 [M+H]$^+$ (calcd for C$_7$H$_9$D$_3$N$_4$O$_2$S, 220.1).

Step 4: Synthesis of Compound (4-(methylcarbamyl)phenyl)carbamic acid t-butyl ester 4-((t-Butoxycarbonyl)amino)benzoic acid (3.0 g, 12.65 mmol) was weighed and placed in a 250 mL single-neck round bottom flask, to which was added 50 mL DMF, and the mixture was stirred at room temperature. Subsequently, EDCI (4.8 g, 25.29 mmol), TEA (4.5 g, 44.28 mmol), methylamine hydrochloride (1.3 g, 18.98 mmol), and DMAP (16.0 mg, 0.13 mmol) were sequentially added to the system. After that, the system was stirred and reacted overnight at room temperature. The next day, when the consumption of raw materials was monitored, ethyl acetate (70 mL) and water (50 mL) were added to the system, and the reaction was stirred vigorously, and stood for separation of the layers. The aqueous phase was back-extracted with ethyl acetate (20 mL*3). The organic layers were combined, washed with water (20 mL*3) and saturated brine (30 mL) respectively, and dried with anhydrous sodium sulfate. The solvent was removed by rotary evaporation to obtain the crude product, which was then separated by column chromatography to obtain (4-(methylcarbamyl)phenyl)carbamic acid t-butyl ester as off-white solid (2.1 g, yield: 66.5%). MS (ESI): m/z 251.2 [M+H]$^+$.

Step 5: Synthesis of Compound 4-amino-N-methylbenzamide trifluoroacetate (4-(Methylcarbamoyl)phenyl)carbamic acid t-butyl ester (500.0 mg, 2.00 mmol) was weighed and placed in a 50 mL single-neck round bottom flask, to which was added 10 mL dichloromethane, and the mixture was stirred at room temperature. After that, trifluoroacetic acid (1 mL) was added to the system, and then, the system was stirred and reacted overnight at room temperature. The next day, TLC indicated the completion of the reaction. The reaction was concentrated to remove the solvent and excess trifluoroacetic acid, and the residual trifluoroacetic acid in the system was removed by multiple rotatory evaporations with dichloromethane, until the system completely became solid, to obtain 4-amino-N-methylbenzamide trifluoroacetate as off-white solid (510.0 mg), which was directly used in the next step, without further purification.

Step 6: Synthesis of Compound 4-((4-chloro-5-(trifluoromethyl)pyrimidin-2-yl)amino)-N-methylbenzamide 2,4-Dichloro-5-(trifluoromethyl)pyrimidine (499.0 mg, 2.30 mmol) was weighed and placed in a 50 mL single-neck round bottom flask, to which were added 1,2-dichloroethane (5 mL) and t-butanol (5 mL), and then the mixture was stirred at room temperature until the reactions were dissolved and the solution became clear. After that, the system was placed in an ice water bath to continue cooling and stirring. After 15 min, zinc bromide (1.4 g, 6.00 mmol) was added to the system. Then, the system was further stirred for 30 min in an ice-water bath. Then, 4-amino-N-methylbenzamide trifluoroacetate synthesized in the previous step and triethylamine (648.0 mg, 6.40 mmol) were added to the system. After the addition, the ice bath was removed, and the system was stirred and reacted overnight at room temperature. The next day, when the reaction was completed by detection, the solvent was removed by rotatory evaporation. Ethyl acetate (30 mL) and water (20 mL) were added to the system, and the reaction was stirred vigorously, and stood for separation of the layers. The aqueous phase was back-extracted with ethyl acetate (10 mL*3). The organic layers were combined, successively washed with water (15 mL*3) and saturated brine (15 mL), and dried with anhydrous sodium sulfate. The reaction was concentrated tinder reduced pressure, to obtain the crude product, which was then separated by column chromatography to obtain 4-((4-chloro-5-(trifluoromethyl)pyrimidin-2-yl)amino)-N-methylbenzamide as off-white solid (280.0 mg, yield: 42.3%). MS (ESI): m/z 331.0 [M+H]$^+$.

Step 7: Synthesis of Compound N-methyl-4-(4-(((3-(N-deuteromethanesulfonamido) pyrazin-2-yl) methyl)amino)-5-(trifluoromethyl)pyrimidin-2-yl) amino)benzamide To a 25 mL single-neck round bottom flask containing N-(3-(aminomethyl)pyrazin-2-yl)-N-deuteromethylmethanesulfonamide (compound 41-3, 65.8 mg, 0.30 mmol), were added 5 mL 1,2-dichloroethane and 5 mL t-butanol, and then the mixture was stirred at room temperature until the reactions were dissolved and the solution became clear. Subsequently, to the system, were added 4-((4-chloro-5-(trifluoromethyl)pyrimidin-2-yl)amino)-N-methylbenzamide (100.0 mg, 0.30 mmol) and diisopropylethylamine (116.3 mg, 0.90 mmol). After the addition, the system was transferred to an oil bath at 80° C. and refluxed for reaction. After 8 h, the complete consumption of raw materials was monitored by TLC. Stop heating, and after the system was cooled to room temperature, the solvent was removed by rotary evaporation to obtain a crude product, which was then separated and purified by Pre-TLC to obtain N-methyl-4-((4-((3-(N-trideuteromethylmethanesulfonamido)pyrazin-2-yl)methyl)amino)-5-(trifluoromethyl)pyrimidin-2-yl)amino)benzamide as off-white solid (compound 41, 12 mg). Yield: 7.8%. MS (ESI) m/z 514.2 [M+H]⁺. ¹H NMR (400 MHz, DMSO-d₆) δ 9.83 (s, 1H), 8.69 (s, 1H), 8.59 (s, 1H), 8.32 (s, 1H), 8.20 (d, J=4.0 Hz, 1H), 7.68-7.61 (dd, J=14.4, 8.4 Hz, 4H), 7.41-7.39 (t, =4.4 Hz, 1H), 5.01 (d, J=3.6 Hz, 2H), 3.20 (s, 3H), 2.76 (d, J=4.0 Hz, 3H).

Using the raw materials corresponding to the compound and the preparative method similar to that of compound 41, compounds 42 and 43 were prepared.

Example 3 Synthesis of N-trideuteromethyl-4-((4-(((3-(N-trideuteromethylmethanesulfonamido)pyrazin-2-yl)methyl)amino)-5-(trifluoromethyl)pyrimidin-2-yl)amino)benzamide (Compound 44) and its Hydrochloride

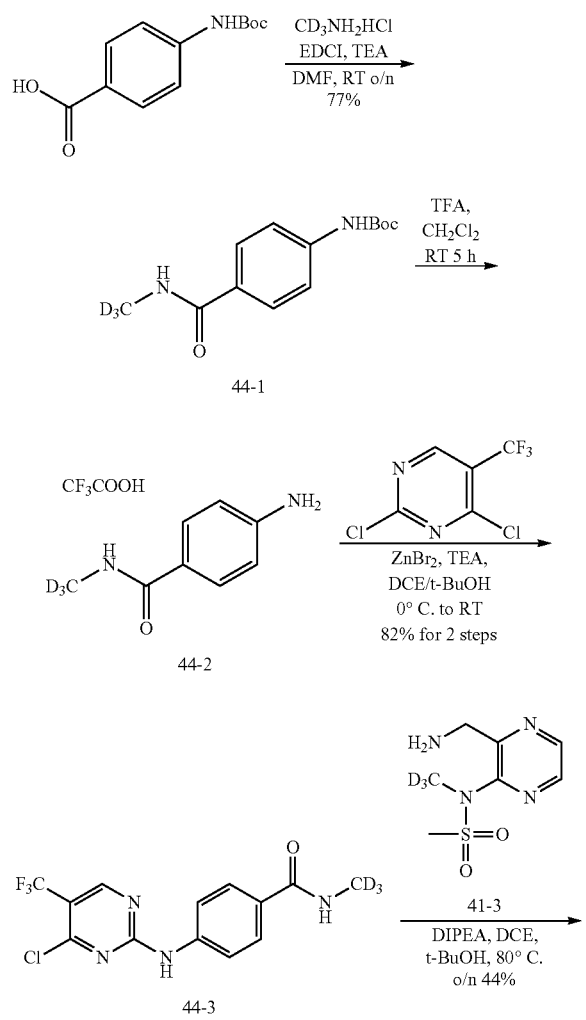

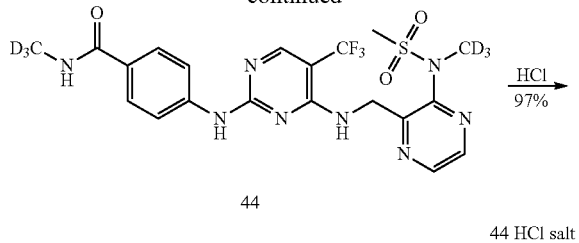

Step 1: Synthesis of (4-(trideuteromethylcarbamoyl)phenyl)carbamic acid t-butyl ester (Compound 44-1)

N-Boc-4-aminobenzoic acid (6.0 g, 25.29 mmol) and EDCI (7.27 g, 37.93 mmol) were respectively weighed and placed in a 250 ml single-neck round bottom flask, and at the same time, DMF (50 mL) was added. The mixture was stirred at room temperature. Subsequently, triethylamine (6.40 g, 63.22 mmol) and deuterated methylamine hydrochloride (1.96 g, 27.82 mmol) were added to the system. After addition, the system was stirred and reacted overnight at room temperature. The next day, the sample was collected and subjected to TLC, and when TLC indicated the completion of the reaction, ethyl acetate (50 mL) and water (50 mL) were added to the system. The reaction was stirred vigorously, and stood for separation of the layers. The aqueous phase was back-extracted with ethyl acetate (50 mL*3). The organic layers were combined, successively washed with water (30 mL*3) and saturated brine (50 mL), and dried with anhydrous sodium sulfate. The reaction was concentrated in vacuo to obtain the crude product, which was then separated and purified by column chromatography to obtain (4-(deuteromethylcarbamoyl)phenyl)carbamic acid t-butyl ester as off-white solid (4.92 g, yield: 76.8%). LC/MS (ESI+): m/z 254.2 [M+H]⁺ (calcd for C₁₃H₁₅D₃N₂O₃, 254.2).

Step 2: Synthesis of 4-amino-N-trideuteromethylbenzamide trifluoroacetate (Compound 44-2)

(4-(Deuteromethylcarbamoyl)phenyl)carbamic acid t-butyl ester (3.0 g, 11.84 mmol) was weighed and placed in a 100 mL single-neck round bottom flask, and at the same time, dichloromethane (15 mL) was added. The mixture was stirred at room temperature. After that, trifluoroacetic acid (7 mL) was added to the system, and then, the system was stirred and reacted at room temperature. After 5 h, the sample was collected and subjected to TLC. TLC indicated the completion of the reaction. The reaction was rotatory evaporated to remove the solvent and excess trifluoroacetic acid, and the residual trifluoroacetic acid in the system was removed by multiple rotatory evaporations with dichloromethane, to obtain 4-amino-N-deuteromethylbenzamide trifluoroacetate as off-white solid, which was directly used in the next step, without further purification.

Step 3: Synthesis of 4-((4-chloro-5-(trifluoromethyl)pyrimidin-2-yl)amino)-N-trideuteromethylbenzamide (Compound 44-3)

2,4-Dichloro-5-trifluoromethylpyrimidine (2.83 g, 13.02 mmol) was weighed and placed in a 100 mL single-neck round bottom flask, to which were added 1,2-dichloroethane (30 mL) and t-butanol (30 mL), and then the mixture was stirred at room temperature until the reactions were dissolved and the solution became clear. After that, the system was placed in an ice water bath to continue cooling and stirring. When the internal temperature of the system was reduced to about 0° C., zinc bromide (8.0 g, 35.52 mmol) was added to the system. Then, the system was further reacted for 30 min in an ice-water bath. Then, 4-amino-N-deuteromethylbenzamide trifluoroacetate synthesized in the previous step and triethylamine (3.83 g, 37.89 mmol) were added to the system. After the addition, the ice bath was removed, and the system was stirred and reacted overnight at room temperature. The next day, the sample was collected and subjected to TLC. TLC indicated the complete consumption of raw materials, and the reaction was terminated. The solvent was removed by rotary evaporation. Ethyl acetate (50 mL) and water (30 mL) were added to the system, and the reaction was stirred vigorously, and stood for separation of the layers. The aqueous phase was back-extracted with ethyl acetate (30 mL*3). The organic layers were combined, successively washed with water (30 mL*3) and saturated brine (30 mL), and dried with anhydrous sodium sulfate. The reaction was concentrated in vacuo, to obtain the crude product, which was separated and purified by column chromatography to obtain 4-((4-chloro-5-(trifluoromethyl)pyrimidin-2-yl)amino)-N-deuteromethylbenzamide as off-white solid (3.23 g). The two-step reaction yield of step 2 to step 3: 81.8%.

LC/MS (ESI+): m/z 334.0 [M+H]$^+$ (calcd for $C_{13}H_7D_3ClF_3N_4O$, 334.0). $^1$H NMR (400 MHz, DMSO-d$_6$) δ 10.89 (s, 1H), 8.87 (s, 1H), 8.31 (s, 1H), 7.84-7.77 (m, 4H).

Step 4: Synthesis of N-trideuteromethyl-4-((4-(((3-(N-trideuteromethylmethanesulfonamide) pyrazin-2-yl)methyl)amino)-5-(trifluoromethyl)pyrimidin-2-yl)amino)benzamide (Compound 44)

4-((4-Chloro-5-(trifluoromethyl)pyrimidin-2-yl)amino)-N-deuteromethylbenzamide (3.1 g, 9.29 mmol) and N-(3-cyanopyrazin-2-yl)-N-deuteromethylmethanesulfonamide (2.0 g, 9.29 mmol) were weighed and placed in a 250 mL single-neck round bottom flask, to which were then added 1,2-dichloroethane (80 ml) and t-butanol (80 mL), and then the mixture was stirred at room temperature until the reactions were dissolved and the solution became clear. Then, diisopropylethylamine (3.6 g, 27.87 mmol) was added to the system. After that, the system was transferred to an oil bath at 80° C., as well as refluxed, stirred, and reacted overnight. The next day, the sample was collected and subjected to TLC. Once TLC indicated the completion of the reaction, the solvent was removed by rotary evaporation. Ethyl acetate (100 mL) and water (50 ml) were added to the system, and the reaction was stirred vigorously, and stood for separation of the layers. The aqueous phase was back-extracted with ethyl acetate (50 ml.*3). The organic layers were combined, successively washed with water (30 mL*3) and saturated brine (50 mL), and dried with anhydrous sodium sulfate. The reaction was concentrated in vacuo, to obtain the crude product, which was separated and purified by column chromatography to obtain the target compound as off-white solid (2.36 g). Then, the solid was placed in a 250 mL single-neck round bottom flask, to which was added ethyl acetate (75 mL), and the mixture was stirred at room temperature to make a slurry. After 3 h, it was subjected to the suction filtration. The filter cake was rinsed with ethyl acetate (45 mL) in a small amount for several times, and then placed in a vacuum drying oven to dry at low temperature, to obtain N-deuteromethyl-4-((4-(((3-(N-deuteromethylmethanesulfonamide)pyrazin-2-yl)methyl)amino)-5-(trifluoromethyl)pyrimidin-2-yl)amino)benzamide (2.11 g) as white solid. Yield: 44.0%. LC/MS (ESI+): m/z 517.2 [M+H]$^+$ (calcd for $C_{20}H_{15}D_6F_3N_8O_3S$, 517.2). $^1$H NMR (400 MHz, DMSO) δ 9.83 (s, 1H), 8.69 (d, J=2.8 Hz, 1H), 8.58 (d, J=2.4 Hz, 1H), 8.31 (s, 11H), 8.17 (s, 1H), 7.67-7.61 (dd, J=15.4, 8.6 Hz, 4H), 7.41 (t, J=5.0 Hz, 1H), 5.00 (d, J=4.8 Hz, 2H), 3.20 (s, 3H).

Step 5: Synthesis of N-deuteromethyl-4-((4-(((3-(N-deuteromethylmethanesulfonamide) pyrazin-2-yl)methyl)amino)-5-(trifluoromethyl)pyrimidine-2-yl)amino)benzamide hydrochloride Compound 44 (500 mg, 0.97 mmol) was weighed and placed in a 100 mL single-neck round bottom flask, to which was added methanol (25 mL), and the mixture was stirred at room temperature. Subsequently, the solution of HCl in ethanol (2.25 ml, 2.0 M) was slowly added dropwise to the system. After that, the system was continued to stir and react at room temperature. After 1.5 h, the system was subjected to the suction filtration, and the filter cake was rinsed with methanol (15 mL) several times in small amounts, and then placed in a vacuum drying oven to dry at low temperature, to obtain N-deuteromethyl-4-((4-(((3-(N-deuteromethylmethanesulfonamide)pyrazin-2-yl)methyl)amino)-5-(trifluoromethyl)pyrimidin-2-yl)amino)benzoyl hydrochloride (517 mg) as off-white solid. Yield: 96.6%. LC/MS (ESI+): m/z 517.2 [M+H]$^+$ (calcd for $C_{21}H_{16}D_6ClF_3N_8O_3S$, 517.2). $^1$H NMR (400 MHz, DMSO) δ 10.02 (s, 1H), 8.68 (d, J=2.8 Hz, 1H), 8.58 (d, J=2.4 Hz, 1H), 8.35 (s, 1H), 8.21 (s, 1H), 7.67-7.57 (n, 5H), 5.26 (br, 6H), 5.00 (d, J=4.8 Hz, 2H), 3.19 (s, 3H).

Example 4 Synthesis of N-deuteromethyl-4-((4-(((3-(N-deuteromethanesulfonamido) pyrazin-2-yl)deuteromethyl)amino)-5-(trifluoromethyl)pyrimidine-2-yl)amino)benzamide (Compound 45)

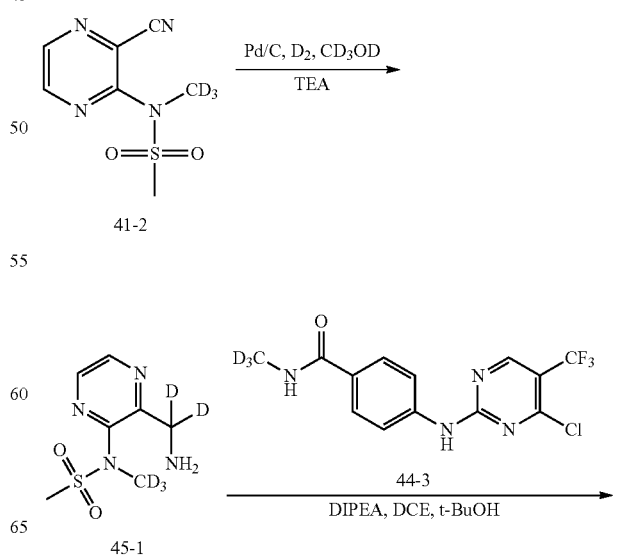

-continued

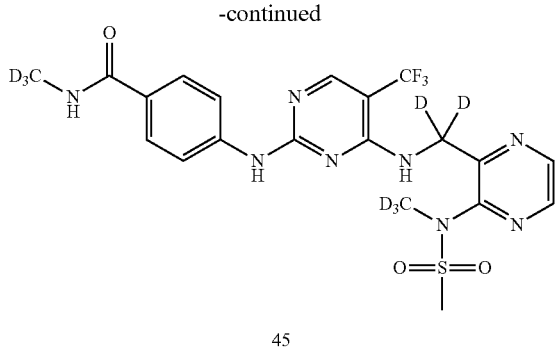

45

Step 1: Synthesis of compound N-(3-(aminodideuteromethyl)pyrazin-2-yl)-N-deuteromethylmethanesulfonamide (45-1)

Compound 41-2 (100.0 mg, 0.46 mmol) was weighed and placed in a 25 mL single-neck round bottom flask, to which was then added 5 mL deuterated methanol (188.2 mg, 1.86 mmol), and then the mixture was stirred at room temperature until the reactions were dissolved and the solution became clear. Subsequently, 20.0 mg of wet palladium-carbon (treated with heavy water) and triethylamine (188.2 mg, 1.86 mmol) were sequentially added to the system. The system was subjected to the operation of deuterium replacement, and the operation was repeated ten times. After that, the system was stirred and reacted at room temperature. After 72 h, the reaction was completed by detection. The system was subjected to the suction filtration. The filter cake was rinsed with deuterated methanol (10 mL) several times in small amounts. The filtrate was combined, and the solvent was removed by rotary evaporation to obtain N-(3-(aminodeuteromethyl)pyrazin-2-yl)-N-deuteromethylmethanesulfonamide as light yellow-brown oily liquid, that was directly used in the next step without further purification. MS (ESI): m/z 222.2 [M+H]$^+$.

Step 2: Synthesis of compound N-deuteromethyl-4-((4-(((3-(N-deuteromethanesulfonamido) pyrazin-2-yl)deuteromethyl)amino)-5-(trifluoromethyl)pyrimidine-2-yl)amino)benzamide (45)

To a 25 mL single-neck round bottom flask containing N-(3-(aminodeuteromethyl)pyrazin-2-yi)-N-deuteromethylmethanesulfonamide (22.1 mg, 0.10 mmol), were added 2 mL of 1,2-dichloroethane and 2 mL of t-butanol, and then the mixture was stirred at room temperature until the reactions were dissolved and the solution became clear. Subsequently, to the system, were added compound 44-3 (33.4 mg, 0.10 mmol) and diisopropylethylamine (30.6 mg, 0.30 mmol). After the addition, the system was transferred to an oil bath at 80° C. and refluxed for reaction. After 8 h, the complete consumption of raw materials was monitored by TLC. Stop heating, and after the system was cooled to room temperature, the solvent was removed by rotary evaporation to obtain a crude product, which was then separated and purified by Pre-TLC, to obtain N-deuteromethyl-4-((4-(((3-(N-deuteromethanesulfonamido)pyrazin-2-yl)methyl)amino)-5-(trifluoro methyl)pyrimidine-2-yl)amino)benzamide as off-white solid (8.1 mg), with a yield of 15.6%. MS (ESI): m/z 519.2 [M+H]$^+$. $^1$H NMR (400 MHz, DMSO-d$_6$) δ 9.83 (s, 1H), 8.69 (d, J=2.0 Hz, 1H), 8.58 (d, J=2.4 Hz, 1H), 8.31 (s, 1H), 8.17 (s, 1H), 7.67-7.61 (dd, J=15.2, 8.8 Hz, 4H), 7.39 (s, 11H), 3.20 (s, 3H).

Example 5 Synthesis of 4-((4-(((3-(N-trideuteromethylmethanesulfonamide)pyrazin-2-yl)methyl)amino)-5-(trifluoromethyl)pyrimidine-2-yl)amino)benzamide (Compound 52)

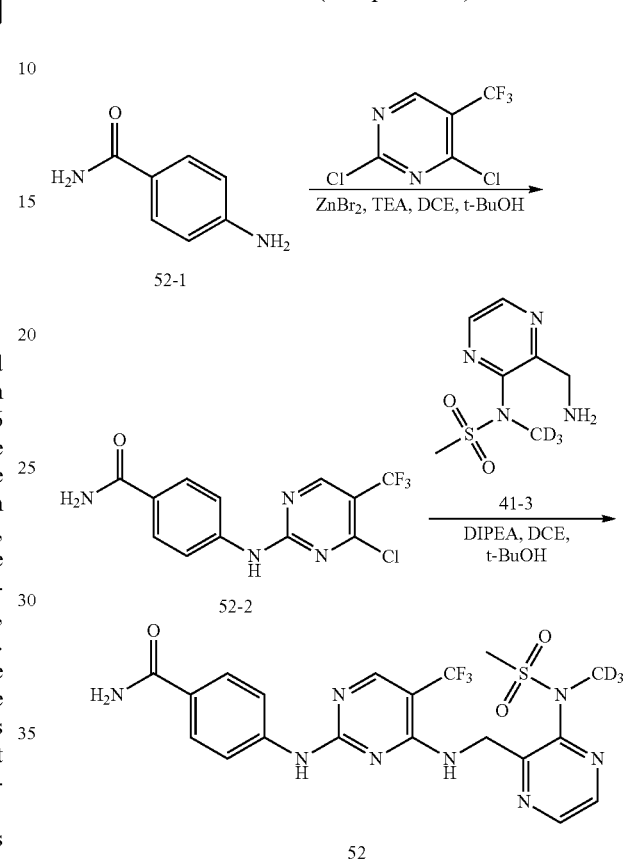

Step 1: Synthesis of compound 4-((4-chloro-5-(trifluoromethyl)pyrimidin-2-yl)amino) benzamide (52-2)

2,4-Dichloro-5-(trifluoromethyl)pyrimidine (434 mg, 2.00 mmol) was weighed and dissolved in a 25 mL single-neck round bottom flask, to which were added 1,2-dichloroethane (5 mL) and t-butanol (5 mL), and then the mixture was stirred at room temperature until the reactions were dissolved and the solution became clear. After that, the system was placed in an ice water bath to continue cooling and stirring. After 15 min, zinc bromide (1.2 g, 5.22 mmol) was added to the system. Then, the system was further stirred for 30 min in an ice-water bath. Then, 4-aminobenzamide (237 mg, 174 mmol) synthesized in the previous step and triethylamine (564 ng, 5.57 mmol) were added to the system. After the addition, the ice bath was removed, and the system was stirred and reacted overnight at room temperature. The next day, when the reaction was completed by detection, the solvent was removed by rotatory evaporation. Ethyl acetate (30 mL) and water (20 mL) were added to the system, and the reaction was stirred vigorously, and stood for separation of the layers. The water phase was back-extracted with ethyl acetate (10 mL*3). The organic phase was combined, successively washed with water (15 mL*3)

and saturated brine (15 mL), and dried with anhydrous sodium sulfate. The reaction was concentrated under reduced pressure, to obtain the crude product, which was then separated by column chromatography to obtain 4-((4-chloro-5-(trifluoromethyl)pyrimidine-2-yl)amino) benzamide as off-white solid (294 mg, yield: 3.4%). MS (ESI): m/z 317.0 [M+H]$^+$.

Step 2: Synthesis of compound 4-((4-(((3-(N-trideuteromethylmethanesulfonamide)pyrazin-2-yl) methyl)amino)-5-(trifluoromethyl)pyrimidine-2-yi) amino)benzamide (52)

To a 25 mL single-neck round bottom flask containing compound 52-2 prepared above, were added 5 mL of 1,2-dichloroethane and 5 mL of t-butanol, and then the mixture was stirred at room temperature until the reactions were dissolved and the solution became clear. Subsequently, to the system, were added compound 44-3 (63.0 mg, 0.20 mmol) and diisopropylethylamine (78 mg, 0.60 mmol). After the addition, the system was transferred to an oil bath at 80° C. and refluxed for reaction. The next day, the complete consumption of raw materials was monitored by TLC. Stop heating, and after the system was cooled to room temperature, the solvent was removed by rotary evaporation to obtain a crude product, which was then separated and purified by Pre-TLC, to obtain 4-((4-(((3-(N-deuteromethylmethanesulfonamide)pyrazin-2-yl)methyl)amino)-5-(trifluoromethyl)pyrimidine-2-yl)amino)benzamide (22 mg) as off-white solid, with a yield of 22.0%. MS (ESI) m/z 500.1 [M+H]$^+$. $^1$H NMR (400 MHz, DMSO-d$_6$) δ 9.83 (s, 1H), 8.69 (s, 2H), 8.60 (s, 1H), 8.31 (s, 1H), 8.20 (d, J=4.0 Hz, 1H), 7.68-7.60 (dd, J=15.4, 8.4 Hz, 4H), 7.41-7.39 (t, J=4.4 Hz, 1H), 5.03 (d, J=3.6 Hz, 2H), 3.20 (s, 3H).

Known compounds 4-amino-3,5-dideuterobenzoic acid and 4-amino-2,6-dideuterobenzoic acid (Journal of Labelled Compounds and Radiopharmaceuticals, 53(11-12), 668-673; 2010) were used as raw materials, and by referring to the methods in the above-mentioned examples, compounds 48 to 50 as well as 53 to 55 were prepared. Using known compound 4-amino-2,3,5,6-tetradeuterobenzoic acid (Journal of Natural Products, 79(6), 1532-1537; 2016) as a raw material, compounds 59 to 61 were prepared by referring to the method in the above examples.

The beneficial effect of the present invention was demonstrated by following experimental examples.

Experimental Example 1 the Inhibitory Activity of the Deuterated Compound of the Present Invention on FAK (1) Experimental Method By referring to literature methods (Cancer Res. 2008, 68, 1935), the experiment of inhibitory activity on FAX enzyme was carried out. The details are as follows: the test compound was diluted to 1000 nM, and then subjected to 1:3 serial dilution with DMSO. 0.1 L of the solution was transferred into a 384-well plate, and 2 replicate wells were set up for each concentration. 5 L of 2 FAK enzyme solution was added, then centrifuged at 1000 rpm for 1 min, and incubated at 25° C. for 15 min. 5 L of 2× substrate solution was added and incubate at 25° C. for 60 min. Then, 5 L of Sa-XL665 solution and 5 μL of TK antibody-Eu3+ were added, and centrifuged at 1000 rpm for 1 min, then incubated at 25° C. for 60 min. Finally, Envision 2104 plate reader was used to read the fluorescence signal, and calculate the half inhibitory concentration IC$_{50}$ of each compound on FAX enzyme. The known FAK inhibitor defactinib was used as a control, (2) Experimental Results The inhibitory activity of each compound against FAK was shown in Table 1. It could be seen that the compound prepared in the present invention could effectively inhibit the activity of FAK enzyme, and compared with the non-deuterated compound defactinib, the deuterated compounds 41 and 45 of the present invention have higher inhibitory activity on FAK enzyme.

TABLE 1

The inhibitory activity of the compound according to the present invention on FAK enzyme.

| Compound | defactinib | 41 | 44 | 45 | 46 |
|---|---|---|---|---|---|
| IC$_{50}$ (nM) | 0.24 | 0.20 | 0.47 | 0.15 | 0.37 |

Experimental Example 2 Pharmacokinetic Test of the Deuterated Compound According to the Present Invention in Rats (1) Experimental Method An appropriate amount of test drug (10 mg) was accurately weighed, and 0.25 ml of N,N-dimethylacetamide (DMA) was first added to dissolve it, then 0.5% sodium carboxymethyl cellulose (CMC-Na) was slowly added to 5 ml. The mixture was sonicated, vortexed, and mixed well. 0.2 ml of the final solution prepared above was taken out and stored at −20° C. for the concentration determination.

After fasted overnight (free drinking water), three healthy adult male SD rats (180-250 g, purchased from Chengdu Dossy Experimental Animal Co., Ltd.) were administered by gavaging with a volume of 5 ml/kg; Prior to administration, as well as 0.5 h, 1 h, 2 h, 4 h, 6 h, 8 h, 12 h, 24 h after administration, 0.1 ml of blood was collected from the retroorbital venous plexus, centrifuged at 4° C. for 5 min to separate the plasma, and stored at −20° C. for testing. Then, LC/MS/MS method was used to determine the concentration of the test compound in the plasma. The known FAK inhibitor defactinib was used as a control.

(2) Experimental Results

TABLE 2

Pharmacokinetic parameters of the compounds according the present invention

| | Pharmacokinetic experiment in rats (PO, 10 mpk) | | | |
|---|---|---|---|---|
| Example No. | Peak time $t_{max}$ (h) | Blood concentration $C_{max}$(ng/mL) | Curve area AUC (ng * h/mL) | half life $t_{1/2}$ (h) |
| defactinib | 0.67 | 643 | 1651 | 1.46 |
| Compound 25 | 0.67 | 1220 | 2843 | 1.75 |
| Compound 44 | 1.67 | 971 | 3741 | 2.46 |

As shown in Table 2, compared with defactinib, the deuterated compounds 25 and 44 prepared in the present invention showed better pharmacokinetics. The compound of the present invention has higher maximum plasma concentration Cmax, higher exposure AUC, and longer half-life. Therefore, the deuterated compound prepared in the present invention will have better application prospects as FAK inhibitors or drugs for treatment of cancer.

Experimental Example 3 Pharmacodynamic Experiment of Deuterated Compound of the Present Invention Combined with PD-1 Inhibitor on Tumor Animal Model 1. MC38 Tumor Model:
(1) Experimental Method
Cell culture: MC-38 cells are cultured in DMEM medium containing 10% fetal bovine serum (FBS). MC-38 cells in logarithmic growth phase were collected, and resuspended in HBSS to a concentration suitable for subcutaneous tumor inoculation in C57BL/6 mice.

Experimental animals: C57BL/6 mice, female, 6-8 weeks old, weighing about 18-20 g, 96 mice, purchased from Beijing Vital River Experimental Animal Technology Co., Ltd.

Tumor cell inoculation: Tumor cells in logarithmic growth phase were collected, and the cell concentration was adjusted to $5\times10^6$/mL with HBSS, then 0.1 mL was subcutaneously inoculated on the right side of each mouse near the back, that is, $5\times10^5$/mouse. Then, the tumor volume was observed and measured. When the average tumor volume of the mice grew to 50-100 mm³, the tumor-bearing mice were randomly grouped according to the tumor volume and administered. The detailed information was shown in Table 3, and the day of grouping and administration was defined as day 0.

Calculation of tumor volume: The mice were sacrificed on the 18th day, the tumor was taken out, the tumor volume was measured, and the tumor inhibition rate of each group was calculated.

TABLE 3

MC38 tumor model grouping, dosing information and tumor inhibition rate.

| Groups | N | Administration | Dosage (mg/kg) | Route of administration | Dosing regimen | Tumor inhibition rate |
|---|---|---|---|---|---|---|
| 1 | 8 | media | — | p.o. | BID × 21 | — |
| 2 | 8 | mPD-1 antibody | 10 | i.p. | BIW × 3 | 23.8% |
| 3 | 8 | Defactinib+ mPD-1 antibody | 50 10 | p.o. i.p. | BID × 21 BIW × 3 | 52.2% |
| 4 | 8 | compound 44 | 50 | p.o. | QD × 21 | 26.9% |
| 5 | 8 | Compound 44+ mPD-1 antibody | 50 10 | p.o. i.p. | QD × 21 BIW × 3 | 55.6% |

Note:
N: number of animals used; i.p.: intraperitoneal injection; p.o.: intragastric administration; BID: twice a day; QD: once a day; BIW: twice a week.

(2) Experimental Results
The pharmacodynamics of animals after 18 days of administration was shown in FIG. 1, and the tumor inhibition rate calculated was shown in Table 3. It could be seen that the efficacy of compound 44 alone was better than that of mPD-1 antibody alone, indicating that the compound of the present invention had therapeutic effect on MC38 tumor model in mice.

In addition, compared with compound 44 alone (group 4) or mPD-1 antibody alone (group 2), the administration of compound 44 in combination with mPD-1 antibody (group 5) achieved a significantly improved inhibitory effect on tumors and played a synergistic effect.

In addition, compared with the administration of Defactinib (50 mg/kg, twice a day) in combination with mPD-1 antibody (group 3), after administration of compound 44 of the present invention (50 mg/kg, once a day) combined with mPD-1 antibody (group 5), the inhibitory effect on tumor was better, and more excellent inhibitory effect on tumor was achieved. That was to say, when used in combination with PD-1 inhibitors, the compound of the present invention at half the dose of Defactinib could achieve better tumor inhibitory effects, indicating that the combination of the compound according to the present invention and PD-1 inhibitors had a significantly better anti-tumor effect on MC38 tumor model than the combination of Defactinib and PD-1 inhibitors.

2. PAN02 Tumor Model
(1) Experimental Method
The PAN-02 cells in the logarithmic growth phase were collected, washed twice with PBS, and then resuspended in pre-cooled PBS for inoculation. The experimental animals were C57BL/6 mice, females, purchased from Beijing Vital River Experimental Animal Technology Co., Ltd. C57BL/6 mice were adapted to the laboratory environment for 3 days. PAN-02 cells were subcutaneously inoculated into the right ribs, and the amount of cells inoculated was $1\times10^6$/mouse. When the tumor grew to about 100 mm³, they will be screened and randomly grouped. Each group included 8 mice. According to Table 4, mice were grouped and administrated as the dosing regimen. The day of grouping and administration was defined as day 1, and the administration period was 33 days.

TABLE 4

PAN-02 tumor model grouping, dosing information and tumor inhibition rate.

| Groups | N | Administration | Dosage (mg/kg) | Route of administration | Dosing regimen | Tumor inhibition rate |
|---|---|---|---|---|---|---|
| 1 | 8 | Media | — | i.g. | — | — |
| 2 | 8 | mPD-1 antibody | 10 mg/kg | i.p. | BIW | 48% |
| 3 | 8 | Defactinib+ mPD-1 antibody | 50 mg/kg 10 mg/kg | i.g. i.p. | BID BIW | 69% |
| 4 | 8 | Compound 44 | 25 mg/kg | i.g. | BID | 66% |
| 5 | 8 | Compound 44+ mPD-1 antibody | 25 mg/kg 10 mg/kg | i.g. i.p. | BID BIW | 83% |

Note:
N: number of animals used; i.p.: intraperitoneal injection; p.o.: intragastric administration; BID: twice a day; QD: once a day; BIW: twice a week.

Figure 2:
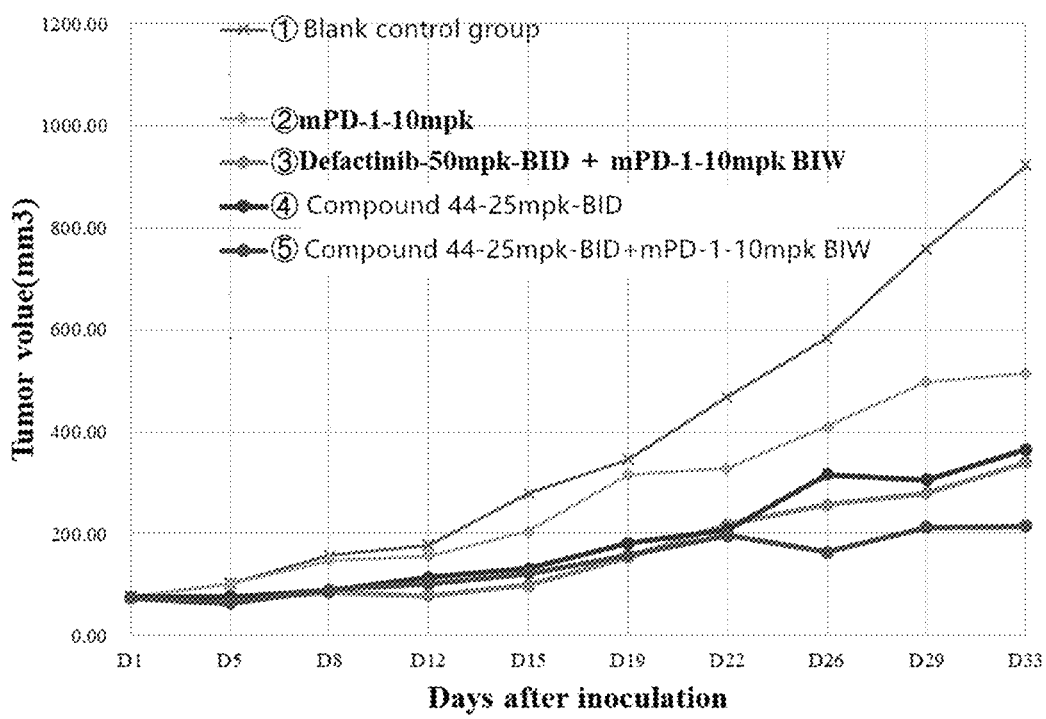
FIG. 2. The pharmacodynamic experiment of the deuterated compound according to the present invention on the PAN02 tumor animal model.

(2) Experimental Results
The pharmacodynamics of animals after 33 days of administration was shown in FIG. 2, and the tumor inhibition rate calculated was shown in Table 4. It could be seen that compared with compound 44 alone (group 4) or mPD-1 antibody alone (group 2), the administration of compound 44 in combination with mPD-1 antibody (group 5) achieved a significantly improved inhibitory effect on tumor.

In addition, compared with the tumor inhibitory effect after administration of Defactinib (50 mg/kg, twice a day) combined with mPD-1 antibody (group 3), the tumor inhibitory effect after administration of compound 44 of the present invention (25 mg/kg, twice a day) in combination with mPD-1 antibody (group 5) was significantly improved. That was to say, when used in combination with PD-1 inhibitors, the compound of the present invention at a lower dose than Defactinib could achieve a more excellent inhibitory effect on tumor, indicating that the administration of the compound according to the present invention combined with PD-1 inhibitors had a significantly better anti-tumor effect on PAN-02 tumor model than the administration of Defactinib combined with PD-1 inhibitors.

In summary, the present invention provided a deuterated compound, and compared with the compound before deuteration, it showed better pharmacokinetics, higher maximum plasma concentration, higher exposure and longer half-life, and had more excellent metabolic performance. Moreover, the deuterated compound of the present invention could effectively inhibit the activity of FAK, and has a very good application prospect in the preparation of FAK inhibitors and/or drugs for treatment of cancer. At the same time, the use of the deuterated compound of the present invention in combination with anti-cancer drugs (such as PD-1 inhibitors) could play a synergistic effect, significantly improve the inhibitory effect on tumors, and provide a better choice for clinical treatment of cancer.

The invention claimed is:

1. A drug combination for the treatment of tumors, comprising:
    a compound or an optical isomer, a tautomer, a pharmaceutically acceptable salt, a prodrug, a hydrate, or a solvate thereof;
    an anticancer drug; and
    a pharmaceutically acceptable carrier,
    wherein said compound and said anticancer drug are in the same or different specification unit preparations for simultaneous or separate administration,
    said anticancer drug is mPD-1 antibody, and
    said compound is selected from the following compounds:

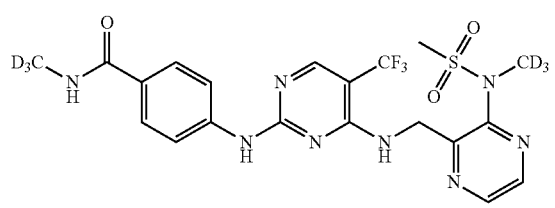

44

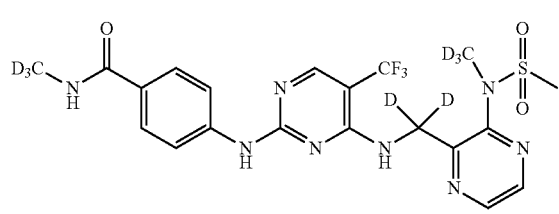

49

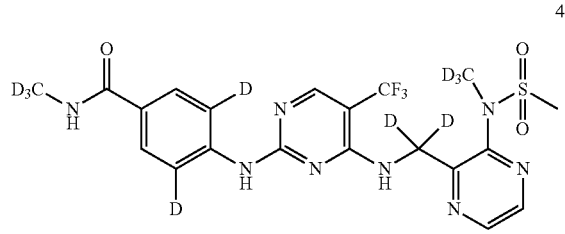

-continued

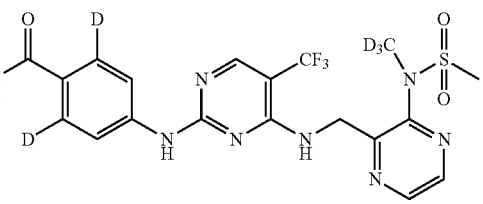

54

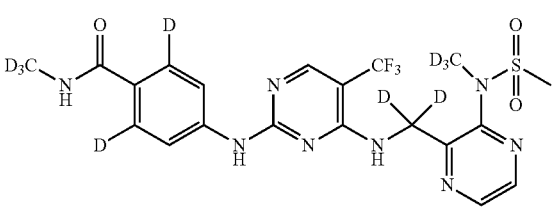

55

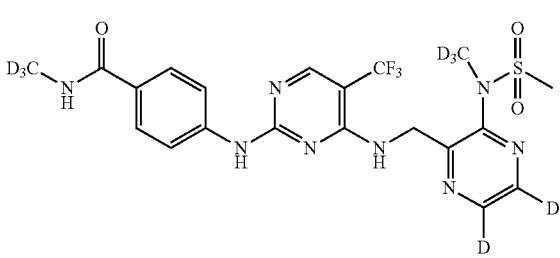

57

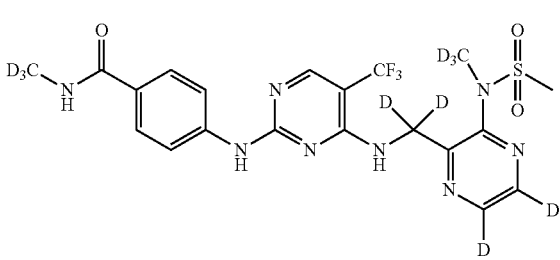

58

60

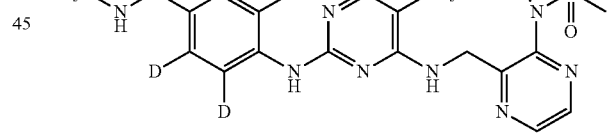

2. The drug combination according to claim 1, wherein said compound is

44

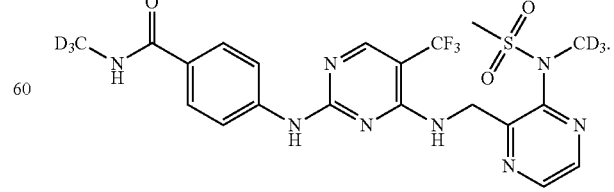

3. A method for preparing a drug combination according to claim 1, comprising providing said compound and said anticancer drug in the same or different specification units for simultaneous or separate administration.

4. A method for treating cancer, comprising administering an effective amount of the drug combination according to claim 1 to a subject in need thereof.

5. The method according to claim 4, wherein said cancer is pancreatic cancer or colon cancer.

* * * * *